United States Patent
Chun et al.

(10) Patent No.: US 9,149,236 B2
(45) Date of Patent: Oct. 6, 2015

(54) ASSESSMENT AND MANAGEMENT OF EMOTIONAL STATE OF A VEHICLE OPERATOR

(71) Applicants: Anthony L. Chun, Los Altos, CA (US); Glen J. Anderson, Beaverton, OR (US); Albert Yosher, Raanana (IL)

(72) Inventors: Anthony L. Chun, Los Altos, CA (US); Glen J. Anderson, Beaverton, OR (US); Albert Yosher, Raanana (IL)

(73) Assignee: Intel Corporation, Santa Clara, CA (US)

( * ) Notice: Subject to any disclaimer, the term of this patent is extended or adjusted under 35 U.S.C. 154(b) by 186 days.

(21) Appl. No.: 13/758,638

(22) Filed: Feb. 4, 2013

(65) Prior Publication Data

US 2014/0218187 A1 Aug. 7, 2014

(51) Int. Cl.
| | |
|---|---|
| *B60Q 1/00* | (2006.01) |
| *A61B 5/00* | (2006.01) |
| *G08B 21/06* | (2006.01) |
| *B60K 28/06* | (2006.01) |
| *G08B 21/02* | (2006.01) |
| *B60K 28/02* | (2006.01) |
| *A61B 5/18* | (2006.01) |

(52) U.S. Cl.
CPC .............. *A61B 5/7264* (2013.01); *A61B 5/0022* (2013.01); *A61B 5/18* (2013.01); *B60K 28/02* (2013.01); *B60K 28/06* (2013.01); *B60K 28/066* (2013.01); *G08B 21/02* (2013.01); *G08B 21/06* (2013.01)

(58) Field of Classification Search
CPC ........ G08B 21/18; G08B 21/06; G08B 21/02; G08B 21/0407; A61B 5/7264; A61B 5/0022; A61B 5/18; B60K 28/06; B60K 28/02; B60K 28/066

USPC ......... 340/439, 576, 436, 425.5; 701/1, 2, 35, 701/29, 29.1; 180/272
See application file for complete search history.

(56) References Cited

U.S. PATENT DOCUMENTS

| | | | |
|---|---|---|---|
| 7,117,075 | B1 * | 10/2006 | Larschan et al. ............. 701/29.6 |
| 8,085,139 | B2 * | 12/2011 | Kanevsky et al. ............ 340/436 |
| 2003/0146841 | A1 | 8/2003 | Koenig | |

(Continued)

FOREIGN PATENT DOCUMENTS

| | | |
|---|---|---|
| EP | 2 093 740 A1 | 8/2009 |
| WO | 2005/042296 A2 | 5/2005 |
| WO | 2014/121182 A1 | 8/2014 |

OTHER PUBLICATIONS

International Search Report and Written Opinion received for PCT Patent Application No. PCT/US2014/014402, mailed on May 14, 2014, 14 pages.

*Primary Examiner* — Anh V La
(74) *Attorney, Agent, or Firm* — Sutherland Asbill & Brennan LLP

(57) ABSTRACT

Devices, systems, and techniques are provided for assessment and management of an emotional state of a vehicle operator. Assessment of the emotional state of the vehicle can include accessing operational information indicative of performance of a vehicle, behavioral information indicative of behavior of an operator of the vehicle, and or wellness information indicative of a physical condition of the operator of the vehicle. In one aspect, these three types of information can be combined to generate a rich group set of data, metadata, and/or signaling that can be utilized or otherwise leveraged to generate a condition metric representative of the emotional state of the vehicle operator. Management of the emotional state can be customized to the specific context of the vehicle and/or the emotional state, and can be implemented proactively or reactively.

29 Claims, 12 Drawing Sheets

(56) References Cited

U.S. PATENT DOCUMENTS

| | | | |
|---|---|---|---|
| 2006/0011399 A1* | 1/2006 | Brockway et al. | 180/272 |
| 2006/0149428 A1* | 7/2006 | Kim et al. | 701/1 |
| 2006/0220915 A1 | 10/2006 | Bauer | |
| 2010/0030434 A1* | 2/2010 | Okabe et al. | 701/48 |
| 2010/0238009 A1* | 9/2010 | Cook et al. | 340/439 |
| 2012/0134547 A1 | 5/2012 | Jung | |
| 2012/0161954 A1* | 6/2012 | Liao et al. | 340/439 |

* cited by examiner

ASSESSMENT AND MANAGEMENT OF EMOTIONAL STATE OF A VEHICLE OPERATOR

BACKGROUND

High stress can lead to incidents of various severities when operating a vehicle. One example is "road rage," in which a driver of a vehicle, typically a car, a motorcycle, or a truck, becomes a road safety hazard because of operating the vehicle under a high-stress condition. Various factors, such as increasing number of vehicles on the road, limited road capacity, and stress sources associated with modern life, tend to exacerbate high-stress conditions that can lead to road rage and/or other stress-induced incidents. Conventional approaches to road safety largely fail to prevent, let alone mitigate, these types of incidents.

BRIEF DESCRIPTION OF THE DRAWINGS

The accompanying drawings are an integral part of the disclosure and are incorporated into the subject specification. The drawings illustrate example embodiments of the disclosure and, in conjunction with the description and claims, serve to explain at least in part various principles, features, or aspects of the disclosure. Certain embodiments of the disclosure are described more fully below with reference to the accompanying drawings. However, various aspects of the disclosure can be implemented in many different forms and should not be construed as limited to the implementations set forth herein. Like numbers refer to like elements throughout.

DETAILED DESCRIPTION

Figure 1:
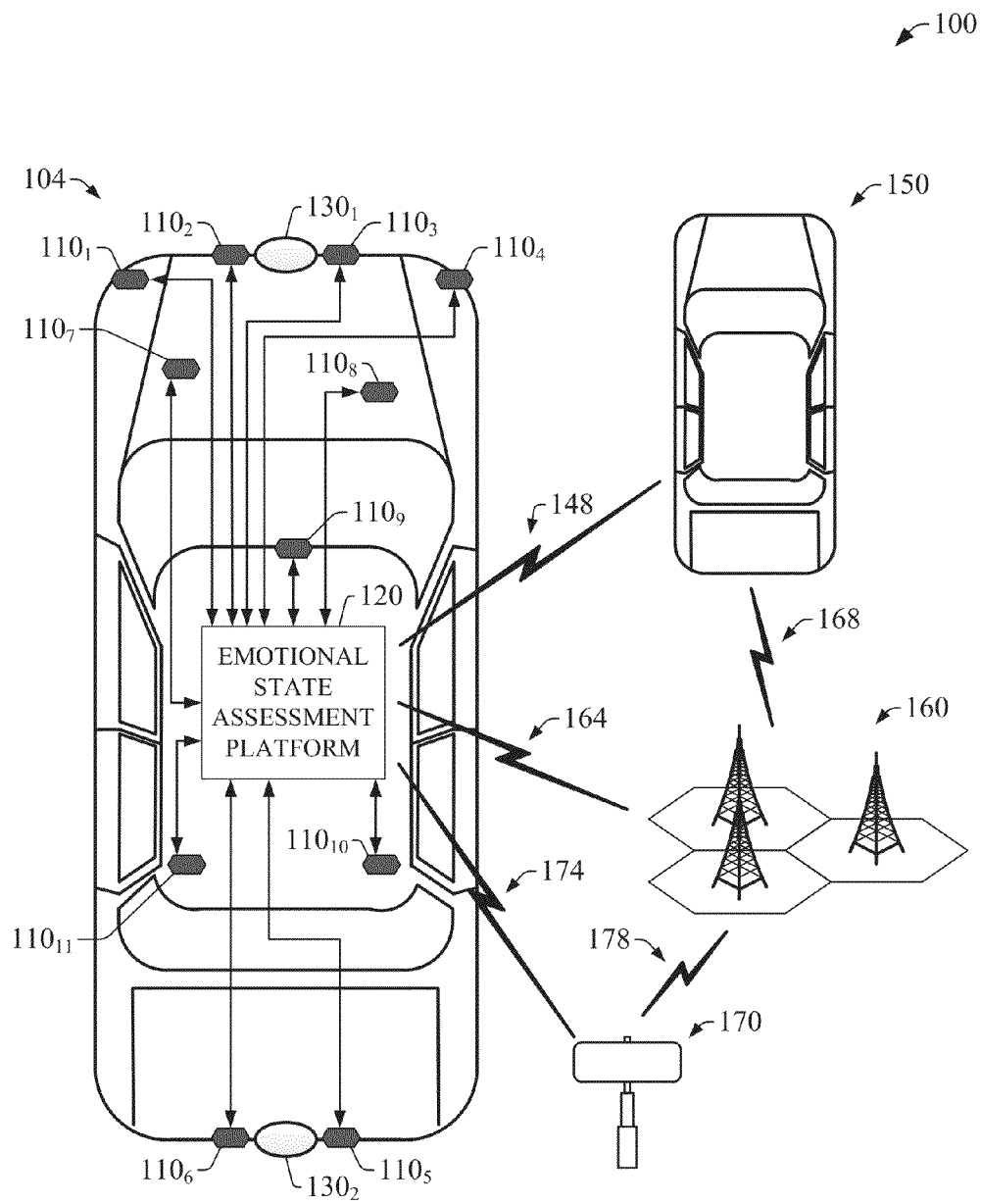
FIG. 1 illustrates an example operational environment in accordance with one or more aspects of the disclosure.

The disclosure recognizes and addresses, in one aspect, the issue of vehicle operator safety under stress conditions. The disclosure can assess the emotional state (also referred to as emotional condition) of an occupant of a vehicle and can convey and/or manage such state in order to at least improve vehicle operator safety. As described in greater detail below, the disclosure provides devices, systems, and techniques for assessment and management of an emotional state of a vehicle operator. A vehicle can refer to a machine with autonomous mobility having an enclosure (e.g., a cabin) that accommodates at least one operator. Such mobility can be provided by a combustion engine, a battery-operated engine, a combination thereof, or the like. The vehicle can include, in certain embodiments, one or more passengers. In the present disclosure, an operator or a passenger of a vehicle is referred to as an occupant of the vehicle. Assessment of the emotional state of the vehicle can include accessing operational information indicative of performance of a vehicle, behavioral information indicative of behavior of an operator of the vehicle, and/or wellness information indicative of a physical condition of the operator the vehicle. In one aspect, these three types of information can be combined or otherwise integrated to generate a rich group of data, metadata, and/or signaling that can be utilized or otherwise leveraged to generate a condition metric representative of the emotional state of the vehicle operator. The emotional state can be conveyed to other vehicle operators by supplying the condition metric. In one scenario, the condition metric can be supplied by rendering it to the operator of the vehicle, wherein the rendering can include conveying a representation of the condition metric in accordance with visual indicia, aural indicia, and/or a haptic stimulus, or a combination thereof. In addition or in the alternative, the condition metric can be supplied to various non-vehicular structures (such as network nodes, roadside billboards, or the like), which can permit generation of a collective emotional state of a group of vehicle operators and management of such state.

Management of the emotional state can be customized to such state and/or a specific context of the vehicle that is operated by a driver in the emotional state, and can be implemented proactively or reactively. In certain scenarios, such management can include configuration of the ambient of the vehicle cabin and/or operation of the vehicle. In other scenarios, management of the emotional state can include generating information of a route suitable for mitigation of high-stress conditions.

At least one example advantage of the disclosure over conventional technology for safety of vehicle operators (e.g., drivers) may be proactive mitigation of road incidents associated with stressed vehicle operators via communication and/or customized management of the emotional state of a vehicle operator. For example, by conveying the emotional state of the vehicle operator to other vehicle operators, awareness of such emotional state can be created on the other vehicle operators such awareness can be referred to as inter-vehicle awareness with the likely ensuing action from these operators directed to reduce the safety hazard posed by a highly-stressed vehicle operator associated with the communicated emotional state.

In connection with customized management of an emotional state of a vehicle operator, feedback of the emotional state to the vehicle operator itself can permit creating intra-vehicle awareness of such state, with likely ensuing action to adjust behavior in order to mitigate, for example, a stress condition or, for another example, to constrain an excitement condition that may lead to distraction and associated safety risk. At least another advantage of customized management of an emotional state is that specific ambient conditions within the vehicle cabin (e.g., temperature condition(s), lighting condition(s), seat configuration(s), a combination thereof, or the like) can be created in response to a specific emotional state of a vehicle operator. For example, an ambient condition can be created via configuration of certain vehicle components. In addition, as yet another example advantage, in scenarios in which the emotional state is indicative of a high-stress condition that poses a safety hazard to the vehicle operator and/or passenger(s) of the vehicle, occupant(s) of other vehicle(s), and/or property, the customized management of such high-stress condition can include automated regulation of the vehicle operation in order to achieve a safe operation condition.

Referring to the drawings, FIG. 1 illustrates an example operational environment 100 in accordance with one or more aspects of the disclosure. As illustrated, the operational environment 100 includes a vehicle 104 that includes a group of sensors 110₁-110₁₁ and an emotional state (ES) assessment platform 120. It should be appreciated that while eleven sensors are depicted, the disclosure is not so limited and contemplates substantially any number of sensors. The group of sensors $110_1$-$110_{11}$ can be deployed (e.g., installed; configured; accepted; installed and accepted; configured and accepted; installed, configured, and accepted; or the like) within the cabin of the vehicle 104 (such as components $110_9$-$110_{11}$) or outside the cabin, including one or more sensors (e.g., sensors $110_7$ and $110_8$) coupled to the engine of the vehicle 104 or other functional elements, such as the brakes or a system functionally coupled thereof (such as the anti-lock brake system), or the engine control unit (ECU). At least a portion of the group of sensors $110_1$-$110_{11}$ can collect or can be configured to collect information (e.g., data, metadata, and/or signaling) indicative of operational features of the vehicle 104. For example, at least one sensor (e.g., one sensor, two sensors, more than two sensors, or the like) of the group of sensors $110_1$-$110_{11}$ can detect or can be configured to detect motion of the vehicle. In such example, the group of sensors $110_1$-$110_{11}$ can include an accelerometer and/or a gyroscope. The accelerometer can detect or otherwise collect and/or supply information indicative of changes in velocity of the vehicle 104, such as increments in velocity or decrements in velocity (also referred to as braking or slowing of the vehicle). It should be appreciated that large magnitude of acceleration can indicate sudden speeding or braking of the vehicle 104. In addition, the gyroscope can detect or otherwise collect and/or supply information indicative of steering the vehicle 104.

At least another portion of the group of sensors $110_1$-$110_{11}$ can collect or can be configured to collect information indicative of behavior of an occupant of the vehicle 104, such as the operator of the vehicle or a passenger of the vehicle. Such information can be referred to as behavioral information (or behavior information) and can comprise, for example, imaging information indicative of an appearance of the occupant of the vehicle, in such example, one or more cameras (e.g., operator-facing cameras, which can be installed in the dashboard area of vehicle 104) can be included in the group of sensors $110_1$-$110_{11}$, and can generate the imaging information. In addition or in the alternative, the behavioral information can comprise audio information indicative of a speech segment uttered by the operator of the vehicle. A microphone that is available (e.g., installed and properly functional) within the cabin of the vehicle (e.g., sensor $110_{11}$) can probe or collect the audio information.

Yet another portion of the group of sensors $110_1$-$110_{11}$ can collect or can be configured to collect information indicative or otherwise representative of physical condition of an occupant (e.g., an operator) of the vehicle 104. Such physical condition can include vitals for the occupant of the vehicle 104, such as blood pressure, blood sugar concentration, heartbeat rate, a combination of the foregoing, or the like. Accordingly, in certain embodiments, the group of sensors $110_1$-$110_{11}$ can include in-cabin sensors (such as medical devices) for probing blood pressure, blood sugar concentration, toxin concentration (e.g., alcohol level), heartbeat rate, and/or pupil dilation. At least some of these in-cabin sensors can be installed, for example, in the steering wheel of the vehicle 104. Information indicative of a physical condition of an occupant of the vehicle 104 can be referred to as wellness information.

It should be appreciated that information indicative of operation of the vehicle and/or behavior of an occupant of the vehicle represents a context of the vehicle 104.

Figure 2:
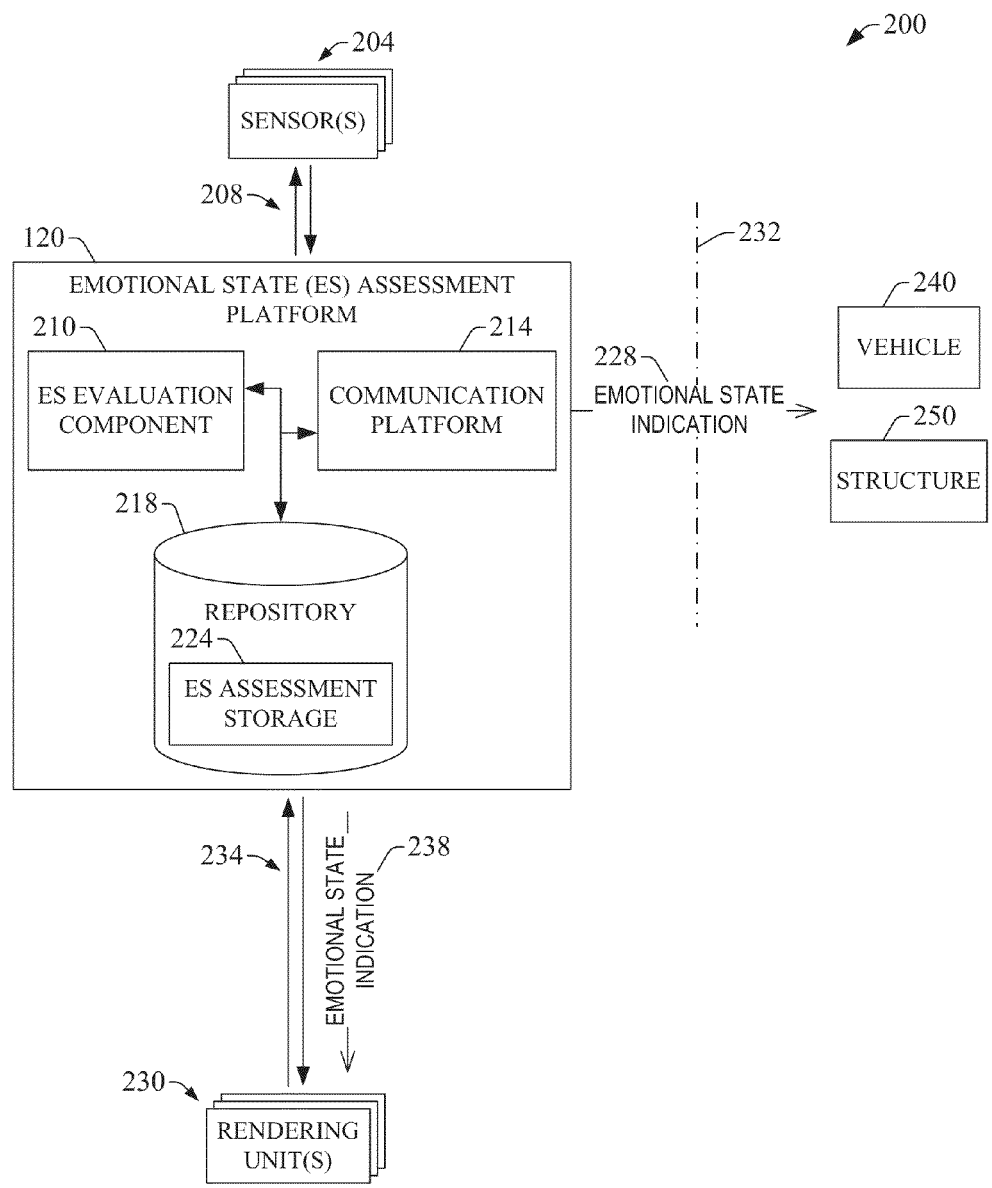
FIG. 2 illustrates an example system in accordance with one or more aspects of the disclosure.

The group of sensors $110_1$-$110_{11}$ can be functionally coupled (e.g., communicatively coupled) to the emotional state (ES) assessment platform 120. Such functional coupling can permit the exchange of information (e.g., data, metadata, and/or signaling) between at least one sensor of the group of sensors $110_1$-$110_{11}$ and the ES assessment platform 120. The information can be exchanged in digital format and/or analogic format. Accordingly, in one aspect, the ES assessment platform 120 can access information indicative of operational features of the vehicle 104 (referred to as operational information) and/or information indicative of behavior of an occupant of the vehicle 104. In addition or in the alternative, the ES assessment platform 120 can access information associated with a physical condition of an occupant of the vehicle 104. In one embodiment, such as example embodiment 200 illustrated in FIG. 2, a group of one or more sensors 204 can be functionally coupled to the ES assessment platform 120 via link(s) 208. The one or more links 208 can comprise wireless link (s), wireline link(s), or any combination thereof and, in certain implementations, can comprise or can be embodied in a vehicle bus, such as a controller area network (CAN) bus (CANbus). The sensor(s) 204 include at least one sensor having the sensing functionality described herein in connection with the sensors $110_1$-$110_{11}$. For instance, the at least one sensor can generate or otherwise acquire behavioral information, operational information, and/or wellness information. In addition, in certain implementations, the sensor(s) 204 can include at least a portion of the sensors $110_1$-$110_{11}$.

Operational information and/or behavioral information that is accessed by the ES assessment platform 120 can be analyzed or otherwise processed in order to refine existing information or to generate additional operational information and/or behavioral information. Thus, in one aspect, the ES assessment platform 120 can access a wealth of rich information indicative or otherwise representative of operation of the vehicle 104 or behavior of its occupants. In one embodiment, e.g., embodiment 200, the ES assessment platform 120 can include a communication platform 214 that can exchange information with at least a portion of the sensor(s) 204 via the link(s) 208, and can persist (e.g., retain and make available) at least a portion of the information in an ES assessment storage 224 within a repository 218. In addition, as illustrated in embodiment 300 shown in FIG. 3A, the communication platform 214 can include an exchange component 324 that can receive and transmit information from and to a sensor of the sensor(s) 204 via the link(s) 208.

The ES assessment platform 120 can analyze or otherwise process imaging information that is received from a camera (e.g., a sensor of the group of sensors $110_1$-$110_{11}$, or a sensor from the sensor(s) 204) to extract specific features from such information. In certain embodiments, such as embodiment 200, the ES assessment platform 120 can include a component, such as ES evaluation component 210, that can analyze or otherwise process the imaging information. As an illustration, the analysis or processing can permit extraction or otherwise determination of one or more facial features of the operator of the vehicle 104. To determine the facial feature, in one aspect, the ES assessment platform 120 can implement at least a facial recognition technique. In addition or in the alternative, it should be appreciated that the ES assessment platform 120 can implement other feature extraction technique(s) in order to determine facial features of the operator of the vehicle 104. In embodiment 200, for example, the ES evaluation component 210 can implement one or more feature extraction techniques.

Moreover or as another alternative, the ES assessment platform 120 can generate gesture information indicative of movement of the operator (e.g., operator's hand(s) movement and/or head movement) of the vehicle 104. In embodiment

200, for example, the ES evaluation component 210 can generate the gesture information. At least a portion of the gesture information that is generated can be indicative or otherwise representative of the emotional state of the operator of the vehicle 104 or any other vehicle that contains the ES assessment platform 120. The ES assessment platform 120 can analyze or otherwise process imaging information obtained by the foregoing camera or other camera contained in the group of sensors $110_1$-$110_{11}$ or sensor(s) 204, and/or by a gesture-sensitive device, such as a touch screen or touch surface. The gesture-sensitive device can be included in the sensor(s) 204, for example. In response to the analysis or processing, the ES assessment platform 120 can determine a gesture of the operator of the vehicle 104 based at least in part on the gesture information. The gesture can be indicative or otherwise representative of the emotional state of the driver. In embodiment 200, for example, the ES evaluation component 210 can determine (e.g., compute) gestures of an operator of a vehicle that contains the ES assessment platform 120 as described herein.

In yet another aspect, the ES assessment platform 120 can analyze or otherwise process audio information received from a microphone (e.g., a sensor of the group of sensors $110_1$-$110_{11}$, or a sensor of the sensor(s) 204) in order to generate, and thus access, behavioral information. As part of the analysis and/or processing, the ES assessment platform 120 can determine a verbal feature of the segment speech based at least in part on the audio information. The verbal feature can be representative of the emotional state of the operator and can include or be embodied in specific words or phrases, such as "he cut me off!" Other verbal features, such as speech portions having certain volume or being delivered in certain manners indicative of stress, also can be determined via the analysis and/or processing. In embodiment 200, for example, the ES evaluation component 210 can determine (e.g., compute) such verbal features of an operator of a vehicle that includes the ES assessment platform 120 as described herein.

Figure 3A:
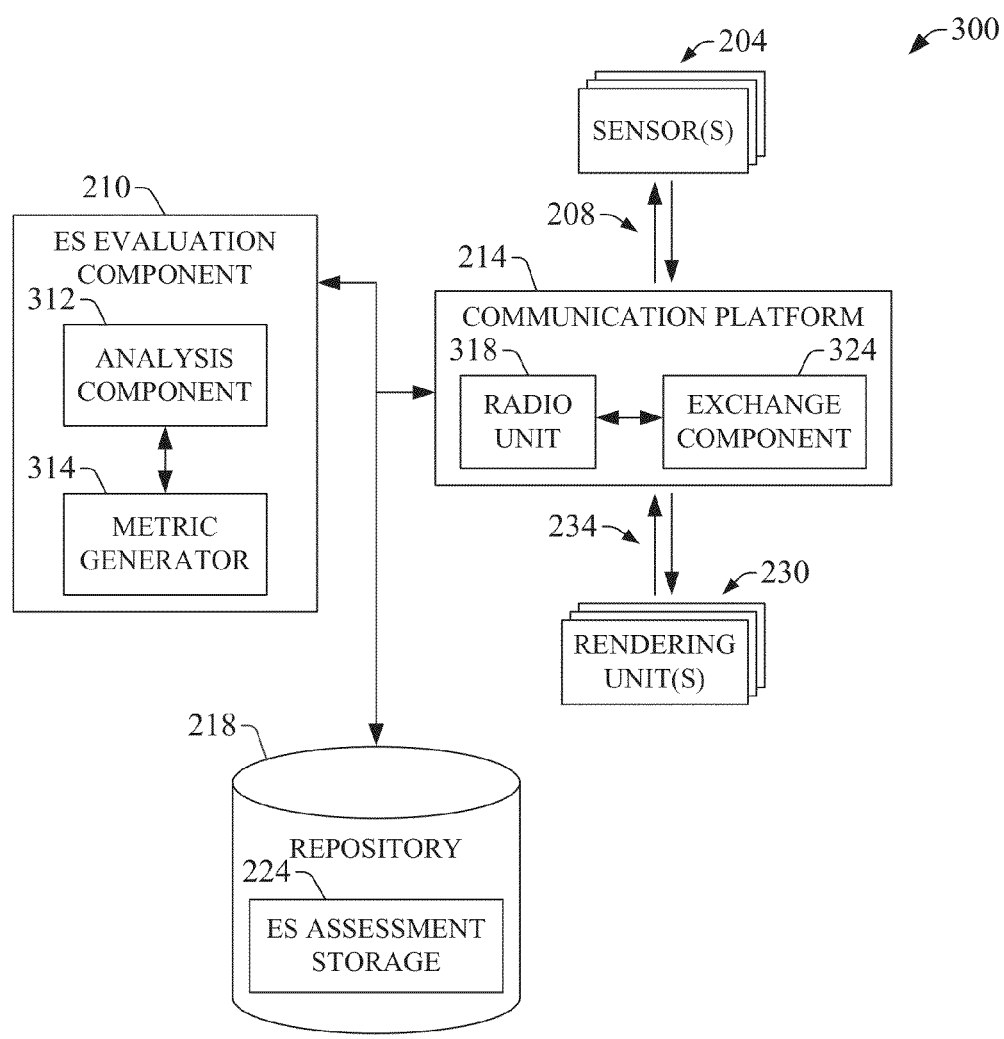
FIGS. 3A-3C illustrate example embodiments of an example system in accordance with one or more aspects of the disclosure.
Figure 3B:
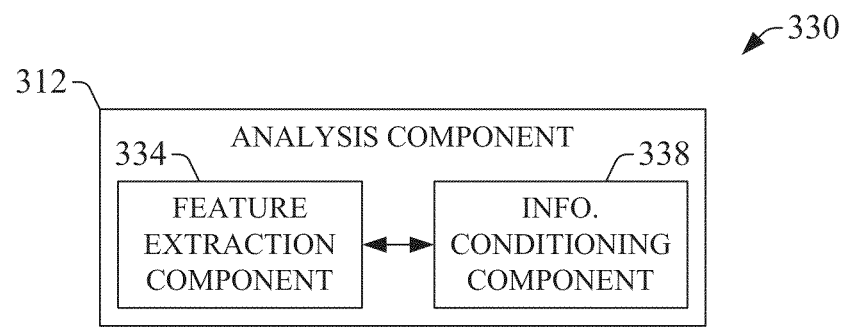

In order to generate or otherwise extract facial features, verbal features, gestures, combinations thereof, or the like, for example, as illustrated in embodiment 300 shown in FIG. 3A, the ES evaluation component 210 can include an analysis component 312 that can implement various feature extraction techniques, such as computerized vision, image processing, and/or speech recognition techniques. In certain implementations, such as embodiment 330 illustrated in FIG. 3B, the analysis component 312 can include a component, such as a feature extraction component 334, that can implement various data mining techniques and related feature extraction techniques that can permit generation of facial features, verbal features, and/or gestures of an operator of a vehicle (e.g., vehicle 104) that includes the ES assessment platform 120 in accordance with one or more aspects described herein. Information such as data structures, metadata objects, and/or algorithms associated with the feature extraction techniques can be retained in the ES assessment storage 224.

The ES assessment platform 120 can determine an emotional state (or emotional condition) of an occupant of the vehicle 104 based at least on operational information, behavioral information, and/or wellness information. In certain embodiments, such as embodiment 200, the ES assessment platform 120 can include a component, such as the ES evaluation component 210, that can determine (e.g., compute or otherwise establish) the emotional state of the occupant of the vehicle 104 based at least on operational information, behavioral information, and/or wellness information. In certain embodiments, the ES assessment platform 120 can utilize or otherwise leverage artificial intelligence (AI) to infer the emotional state and thus determine it. The emotional state that is so determined can be classified in to a category within a predetermined classification of emotional conditions (e.g., happiness state, excitement state, stress state, high-stress state, or the like). Artificial intelligence can be implemented via various techniques that permit identification of a specific context or action, or generation of a probability distribution of specific states of a system without human intervention. In certain implementation, the AI can comprise advanced mathematical algorithms e.g., decision trees, neural networks, regression analysis, cluster analysis, genetic algorithm, and reinforced learning—that can be applied to specific information associated with an operation environment, such as a system or a platform. In connection with inferring an emotional state of an occupant of a vehicle in accordance with aspects of the disclosure, the ES assessment platform 120, or the ES evaluation component 210, for example, can utilize at least one of numerous methodologies for learning from information (e.g., data and/or metadata) and then generating inferences from the models so constructed, e.g., Hidden Markov Models (HMMs) and related prototypical dependency models; more general probabilistic graphical models, such as Bayesian networks created by structure search using a Bayesian model score or approximation; linear classifiers, such as support vector machines (SVMs); non-linear classifiers, such as methods referred to as "neural network" methodologies, fuzzy logic methodologies; and the like.

Determination of the emotional state via inference can include a training (or learning) process that can be implemented prior to deployment (e.g., installation and acceptance) of the ES assessment platform 120 and/or during utilization of the ES assessment platform 120. For example, at least a portion of operational information, behavioral information, and/or wellness information can be processed via an initial training procedure based on correlation, pattern matching, machine learning, and/or other algorithm(s). Such a training process can include a confirmation phase or stage in which confirmation of an initial assessment can be effected. The confirmation phase can permit adaptation or refinement of the training process. The training process and the AI techniques can be retained in a repository that is integrated into or functionally coupled to the ES assessment platform 120 or a component thereof. As illustrated in embodiment 300, the training process and such techniques can be retained in the ES assessment storage 224 in repository 218.

As an illustration of the training process, in certain embodiments, a user interface at the vehicle 104 or any other vehicle having the ES assessment platform 120 can prompt an occupant of the vehicle to confirm a certain emotional state (e.g., anger or happiness) and, in response, the ES assessment platform 120 can collect information that validates or rejects an initial assessment of such emotional state. In one embodiment, the user interface can utilize or otherwise leverage text-to-speech or speech recognition as follows: The vehicle 104 can inquire as follows: "Occupant, are you angry now?" To which the occupant (e.g., the driver of the vehicle 104) can respond "Yes" or "No" via a touch-screen interface, a microphone, or the like. Such responses can permit validation or rejection of the initially assessed state of anger.

In certain implementations, the ES assessment platform 120 can generate a condition metric representative or otherwise indicative of an emotional state of the operator based at least in part on one or more of at least a portion of the operational information, at least a portion of the behavioral information, and at least a portion of the wellness information. To at least such end, in embodiment 300, for example, the analysis component 312 can supply one or more behavioral features of at least the portion of the behavioral information and/or one or more wellness features of at least the portion of the wellness information. In addition, the analysis component 312 can integrate (or fuse some or all of the available features (either behavioral feature(s) or wellness feature(s), or both) with at least the portion of the operational information to form contextual information indicative or otherwise representative of the context of the vehicle 104. Such information is herein referred to as vehicular context information. To integrate such features, the analysis component 312 can aggregate, or apply one or more operations to, at least one of the available features. In certain embodiments, e.g., embodiment 330 shown in FIG. 3B, the analysis component 312 can include an information (info.) conditioning component 338 that can implement such integration, which also can be herein referred to as information fusion. In addition, in certain implementations, the ES assessment platform 120 can infer an emotional state from at least a portion of the contextual information, and can categorize the emotional state according to a predetermined classification as described herein. A category representative of the emotional state can be assigned a metric (e.g., a quantitative metric, a semi-quantitative metric, or a qualitative metric) which can embody or contain the condition metric.

The vehicular context information can be rich in details associated with performance of the vehicle 104 and a relationship between such a performance and a condition of the operator thereof. It should be appreciated that, in one aspect, such relationship can associate the condition of the operator with an ensuing response of the vehicle, as represented by the performance thereof. Accordingly, for example, the effect(s) of the condition of the operator on road safety can be contemplated based at least on performance of the vehicle. At least a portion of the contextual information can be retained in suitable storage e.g., the ES assessment storage 224). The analysis component 312 can supply at least a portion of the contextual information to a metric generation component 314 (or metric generator 314) that, based at least on the portion of the contextual information, can generate the condition metric indicative or otherwise representative of the emotional state of the operator of the vehicle 104. The condition metric can be qualitative, semi-quantitative, or quantitative and can be retained in suitable storage (e.g., the ES assessment storage 224).

Availability of the wellness information (also referred to as biometric information) can be utilized or otherwise leveraged to refine and/or validate a specific emotional state of the occupant of the vehicle 104 that may be determined in accordance with at least the operational information and/or the behavioral information. As an illustration, for an operator of the vehicle 104, the ES assessment platform 120 can correlate certain speech features (such as loud utterances) with certain physical condition(s) (such as elevated blood pressure and/or dilated pupil(s)) in order to validate a previously determined emotional state.

The ES assessment platform 120 can convey the emotional state to an occupant of the vehicle 104, to another vehicle or an occupant therein, and/or to a specific structure (such as a base station, a billboard, a toll booth, or the like) within an environment of the vehicle 104. For example, the ES assessment platform 120 can convey an emotional state indication 238 (e.g., a data object or other information structure) indicative of otherwise representative of the emotional state to at least one of the rendering unit(s) 230. A visual, aural, or haptic representation of such indication can be consumed by an end-user or an end-user device (not depicted) functionally coupled to the ES assessment platform 120. For another example, the ES assessment platform 120 can convey an emotional state indication 228 (e.g., a data object or other information structure indicative of otherwise representative of the emotional state to a vehicle 240 and/or a structure 250. The vehicle 240 and structure 250 can be external to the vehicle 104, as illustrated by a dot-dashed line 232. At least to convey such a state, the ES assessment platform 120 can supply a condition metric indicative or otherwise representative of the emotional state, wherein the condition metric can be generated (e.g., computed or otherwise determined) or received by the ES assessment platform 120. In one aspect, such a metric can embody or can comprise at least one of the ES indication 228 or 238. In one aspect, the ES assessment platform 120 can direct (e.g., transmit an instruction to) one or more rendering units to render at least one of a visual representation of the condition metric, an aural representation of the condition metric, or a haptic representation of the condition metric. It certain scenarios, the specific representation that is rendered can be specific to the specific condition (e.g., excited, stressed, highly stressed, etc.) that is represented by the emotional state. For instance, a visual representation can be utilized for a stress condition, whereas a haptic representation or aural representation can be utilized for a high-stress condition. Such selection may ensure that an occupant (e.g., an operator or a passenger) of the vehicle is more likely aware of the emotional state. The rendering units (e.g., rendering unit(s) 230) can be attached to or integrated into a specific portion of the vehicle, where at least a portion of a rendering unit can be situated in the exterior of the vehicle 104—such as display unit $130_1$ and/or display unit $130_2$—or the interior thereof. For instance, one or more rendering units can be integrated into the dashboard or the seat of a vehicle and can permit rendering visual, aural, and/or haptic representation(s) of a condition metric to an operator associated therewith in order to provide bio-feedback to the operator. Availability of the bio-feedback can raise awareness of the emotional state in the operator and, thus, can permit the operator to control or otherwise adjust the emotional state and/or a physical state of the operator. As illustrated in embodiment 300 in FIG. 3A, the rendering units can be embodied in or can comprise one or more rendering units 230 that can be functionally coupled to the communication platform 214 via link(s) 234. Similarly to link(s) 208, the one or more links 234 can comprise wireless link(s), wireline link(s), or any combination thereof and, in certain implementations, can comprise or can be embodied in a vehicle bus, such as a CANbus. In certain implementations, wireless communication between a rendering unit of the rendering unit(s) 230 can be accomplished via at least the radio unit 318, and wireline (or tethered) communication between another rendering unit of the rendering unit(s) 230 can be accomplished via at least the exchange component 324.

In certain implementations, the ES assessment platform 120 can convey the emotional state on nearly realtime in response to determination of the emotional state. In other implementations, the ES assessment platform 120 can convey the emotional state at specific instants. For instance, the emotional state of an operator of the vehicle can be conveyed (e.g., updated) periodically or according to a schedule. In yet other implementations, the ES assessment platform 120 can convey the emotional state conditionally, or in response to a specific event, such as in response to a request of an occupant or a third party, availability of sufficient computational resources (bandwidth, processing power, or the like) at the vehicle for communication of such state, or specific state represented or indicated by the emotional state. For example, in a scenario in which the emotional condition of an operator of a vehicle is deemed to satisfy a specific criterion (e.g., a hazard criterion, a criterion that defines a level of excitement of the operator, or the like), the ES assessment platform 120 can convey the emotional state. It should be appreciated that, as described herein, the emotional state can account for the mental state of an occupant of the vehicle and the performance of the vehicle.

In addition, as illustrated in embodiment 400, the ES evaluation component 210 can include a feedback component 410 that can configure or otherwise control a feedback rendering component 420 that can be integrated into a portion of the interior of the vehicle for which an emotional state is assessed. The feedback component can be functionally coupled to the communication platform 214 via one or more links 414, which can be embodied in or can comprise wireline link(s), wireless link(s), a combination thereof or the like, and in certain implementations, can comprise or can be embodied in a vehicle bus, such as a CANbus. In certain embodiments, the feedback component 410 can direct the feedback rendering component 420 to prompt an occupant of a vehicle that includes the ES assessment platform 120 to implement a specific action. To at least such end, for example, the feedback component 410 can generate signaling that instructs the feedback rendering component 420 to render information that requests or otherwise prompts an operator or other occupant of the vehicle to effect the specific action. The feedback component 410 can configure or otherwise control the feedback rendering component 420 as described herein in response to a specific state represented or otherwise indicated by an emotional state determined by the ES evaluation component 210. For example, the feedback component 410 can direct the feedback rendering component 420 to convey specific information in response to the emotional state satisfying certain feedback criterion. Feedback criteria can be retained in feedback storage 430 or any repository integrated into or coupled to the feedback component 410. As described herein, for example, the feedback rendering component 420 can be integrated into a seat of an occupant of the vehicle in order to provide a haptic stimulus or other type of stimulus (e.g., an amount of heat) indicative or otherwise representative of such state. As illustrated, the feedback rendering component 420 can be a dedicated component distinct from a rendering unit of the group of rendering unit(s) 230, and can exchange information (e.g., data, metadata, and/or signaling) with the communication platform 214. Such exchange can occur in response to communication of a configuration instruction or a directive from the feedback component 410.

In certain scenarios, the ES assessment platform 120 can direct a rendering unit (e.g., one of rendering unit(s) 230) to provide indicia indicative or otherwise representative of the condition metric. For instance, a condition metric can be categorized according to a classification of emotional states and, in response, assigned a specific color representative of the condition metric and associated emotional state. The classification can include a plurality of categories of emotional states (such as "highly-stressed," "stressed," "non-stressed") and each of the plurality of categories can have a respective color (such as red, representing a highly-stressed state; yellow, representing a stressed state; and green, representing a non-stressed state). In such illustrations, a highly-stressed state can comprise certain level of anger. Accordingly, for example, in such state, the operator of the vehicle 104 can be deemed to be angry. In addition, a "stressed" state can comprise certain level of confusion. Thus, for example, an operator of the vehicle 104 who is determined to be in such state can be deemed to be confused. Moreover, a non-stressed state can comprise certain level of happiness. Accordingly, for example, an operator in such state can be deemed to be happy. It should be appreciated that indicia other than colors can be utilized to represent a condition metric indicative or otherwise representative of an emotional state. For instance, a numeric scale can be contemplated. In various embodiments, a plurality of thresholds (e.g., numeric or otherwise) can define the boundaries for the various categories present in a classification. Thus, in one aspect, a condition metric that exceeds a threshold can indicate that the occupant of the vehicle associated with the emotional state represented or otherwise indicated by the condition metric has transitioned into a different emotional state. Such transition can be, for example, a transition to an emotional state representative of higher stress or lower stress. In one aspect, the higher the threshold that is exceeded, the higher the risk is that the occupant of the vehicle poses a road safety hazard.

The ES assessment platform 120 can utilize or otherwise leverage wireless communication to convey an emotional state of an operator of a vehicle (e.g., vehicle 104) to other vehicles or to various structures, and/or to receive information indicative of an emotional state of one or more respective vehicles. As illustrated in example operational environment 100, the ES assessment platform 120 can communicate wirelessly with a vehicle 150 and/or a structure 170 via wireless link(s) 148 and link(s) 174, respectively. Each of the wireless link(s) 148 and 174 can comprise wireless links formed according to a point-to-point or a line-of-sight radio technology, such as near field communication (NFC) or Bluetooth. In addition or in the alternative, the ES assessment platform 120 can communicate with the vehicle 150 and/or the structure 170 through a wireless network 160. Wireless link(s) 164 can permit functional coupling (e.g., communicative coupling) between the ES assessment platform 120 and the network 160 and or component(s) thereof. As illustrated, the vehicle 150 can communicate with one or more of the network(s) 160 via link(s) 168, which can be embodied in wireline link(s), wireless link(s), a combination thereof or the like.

Wireless communication between the ES assessment platform 120 and the network 160 can be implemented (e.g., processed) in accordance with various radio technology protocols (e.g., 3rd Generation Partnership Project (3GPP), Universal Mobile Telecommunication System (UMTS), 3GPP Long Term Evolution (LTE), Wi-Fi, Worldwide Interoperability for Microwave Access (WiMAX), or the like). In view of such wireless communication, in one aspect, the ES assessment platform 120 can transmit a condition metric indicative or otherwise representative of the emotional state to the vehicle 150 and/or the structure 170 (e.g., infrastructure, such as an access point located within a tower or a billboard; a toll booth; or the like). As illustrated, the structure 170 can communicate with one or more of the network(s) 160 via link(s) 178, which can be embodied in wireline link(s), wireless link(s), a combination thereof, or the like.

In certain scenarios, for example, a vehicle (e.g., vehicle 150) can receive wirelessly, for example) one or more condition metrics from one or more vehicles. At least one condition metric of the one or more condition metrics can be representative of an emotional state of a specific vehicle of the one or more vehicles. At least a portion of the one or more condition metrics that are received can be rendered in various manners at the vehicle. For instance, the vehicle can receive a plurality of condition metrics from a plurality of vehicles, where each condition metric of the plurality of condition metrics can be representative of an emotional state of a respective vehicle of the plurality of vehicles. The plurality of condition metrics can represent a collective emotional state of a plurality of respective operators of the plurality of vehicles, and can be rendered in various manners. For example, two or more of those metrics can be rendered at a dashboard or a navigation display panel of the vehicle (e.g., vehicle 104 or vehicle 150). For another example, two or more of the plurality of condition metrics can be displayed in conjunction with a visual representation of a traffic condition, such as a traffic map, associated with a geographic area containing the plurality of vehicles.

In certain embodiments, the ES assessment platform 120 can communicate a condition metric indicative or otherwise representative of the emotional state of an operator of a vehicle (e.g., vehicle 104) via a link tethered to another vehicle or to infrastructure. The link can be embodied in or can comprise a coaxial cable, an optical fiber, a twisted-pair cable (e.g., category 5 (Cat5) cable), a combination thereof, or the like. Such wireline or non-wireless communication can utilize or otherwise leverage one or more interfaces for functional coupling (e.g., communicative coupling) between the vehicle 104 having the ES assessment platform 120 and another vehicle or a device that can receive the condition metric. The one or more interfaces can include a registered jack (RJ, such as RJ11, RJ14, etc); an RS232 connector; a universal serial bus (USB) connector (e.g., standard USB connector or micro USB connector); a high-definition multimedia (HDMI) connector (such as an HDMI1 connector); combinations of the foregoing; and the like.

It should be appreciated that, in one aspect, communication or otherwise display of an emotional state of the operator of a vehicle to other vehicles can permit raising awareness of such state in the occupant(s) of the other vehicles. Raising awareness can permit operators of the other vehicles to respond to or otherwise adapt their operation behavior to the vehicle that conveys the emotional state. As an illustration, in a scenario in which a vehicle conveys a stressed state or a highly-stressed state, nearby drivers may modify their driving behavior by following the vehicle less closely or letting it merge into a lane or street in response to such states. As another illustration, in a scenario in which a vehicle conveys an emotional state of anxiety or confusion for example, unfamiliarity of the driver of the vehicle with these roads may have created such state nearby drivers may permit such driver to "cut in" to traffic more readily and/or safely. In addition, particularly, yet not exclusively, in scenarios in which the emotional state is a highly-stressed state, communication of the emotional state can permit apprising authorities and/or law enforcement of the emotional condition of the operator of the vehicle. Thus, it is readily apparent, in one aspect, that generation and/or communication of contemporaneous emotional state of an operator of a vehicle can permit mitigation or avoidance of stress-induced road incidents.

Figure 5:
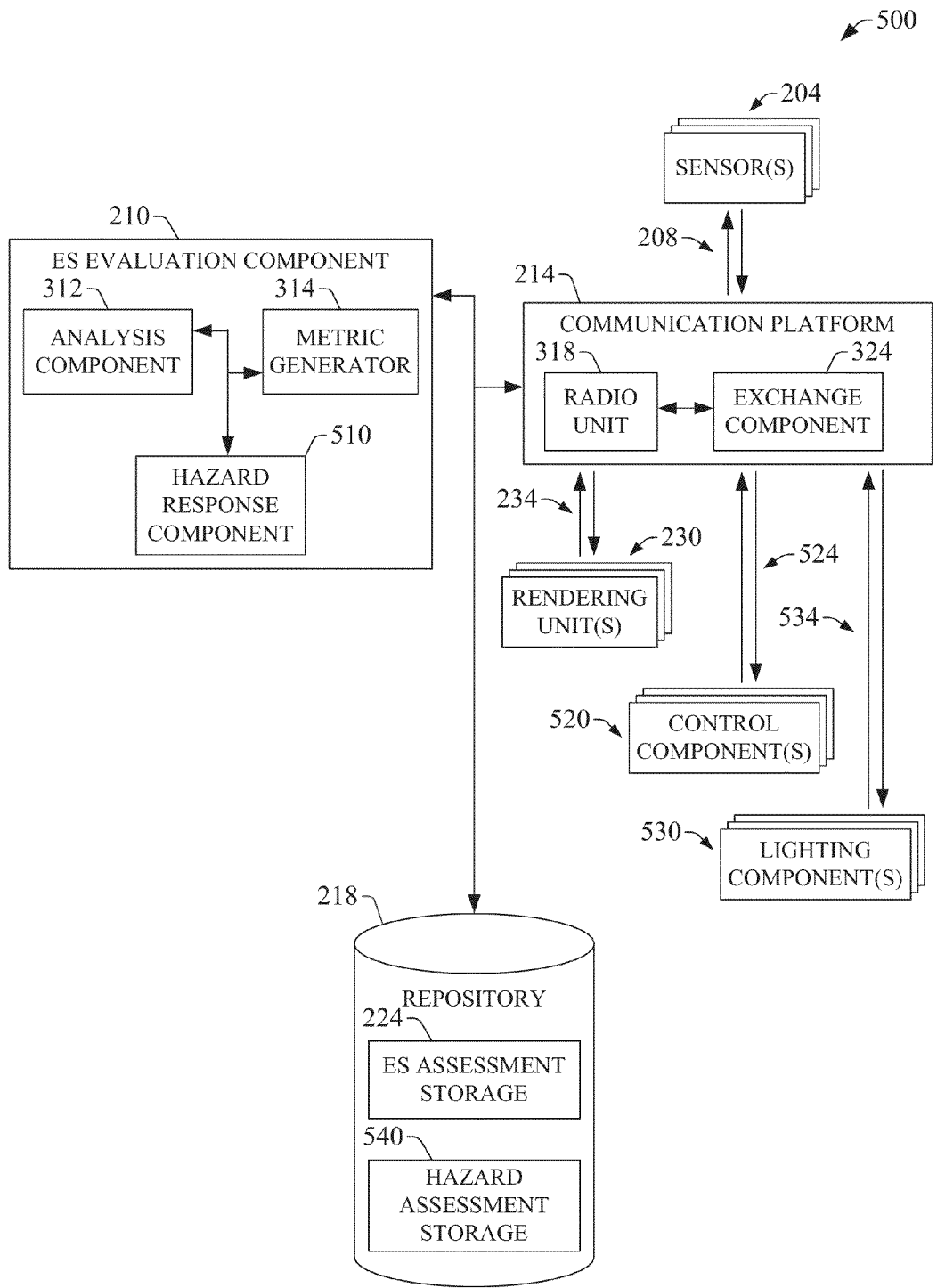
Figure 6:
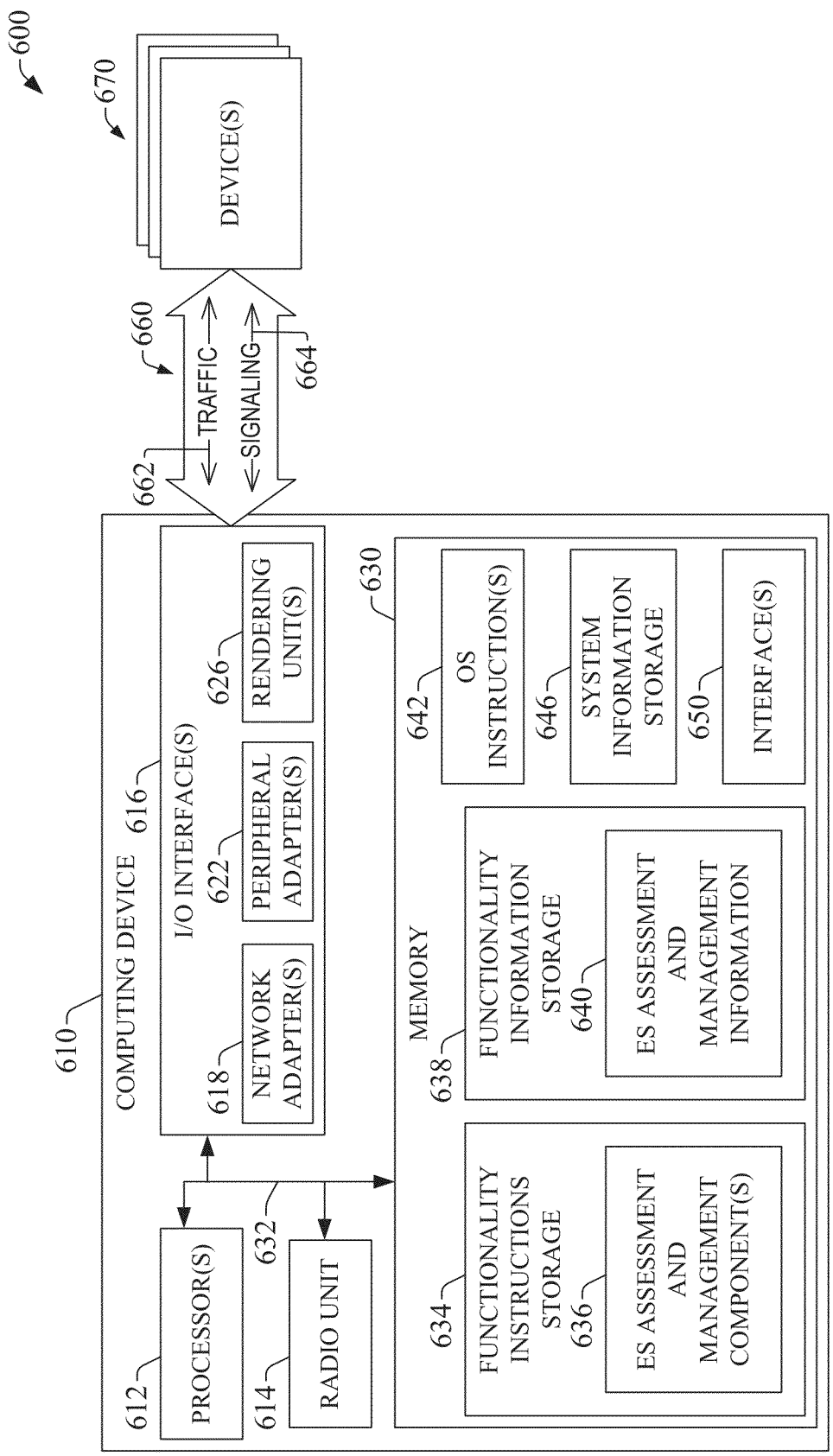
FIGS. 6-9 illustrate various example operational environments in accordance with one or more aspects of the disclosure.
Figure 7:
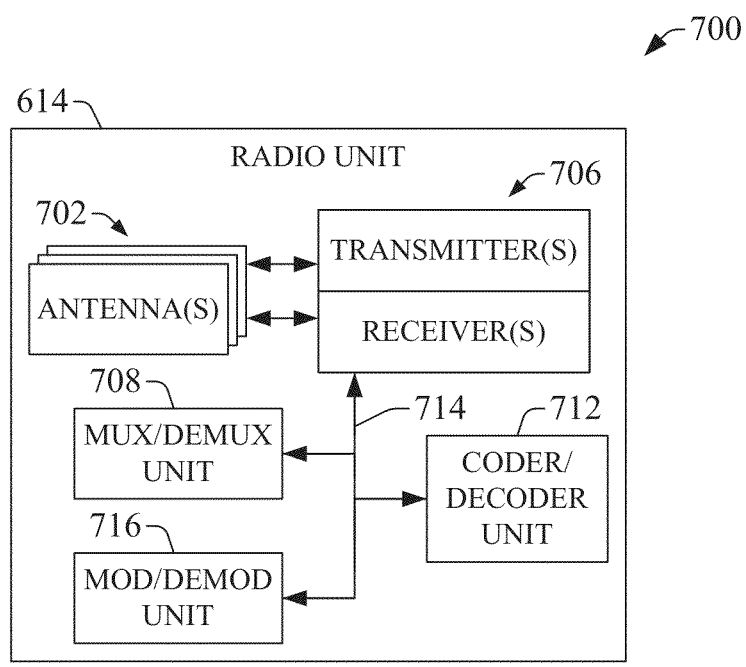
Figure 8:
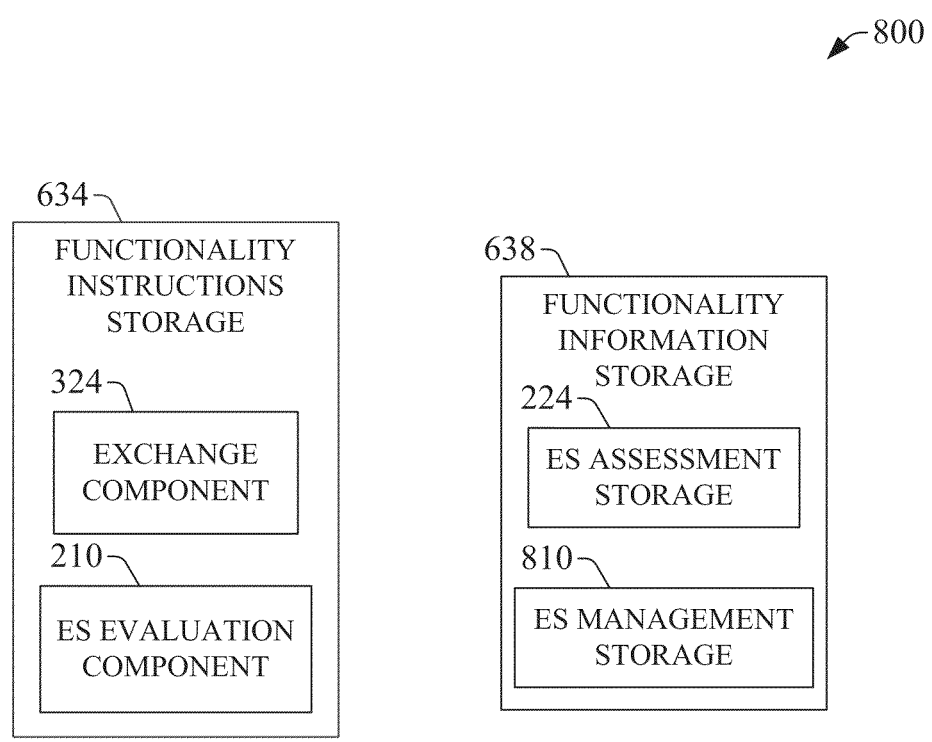

The disclosure permits active management of emotional conditions that may present a road safety hazard. In certain embodiments, the ES assessment platform 120 can generate or otherwise acquire a condition metric representative of an emotional state of a vehicle (e.g., vehicle 104 or vehicle 150). The ES assessment platform 120 can analyze the condition metric and can determine if the condition metric satisfies a vehicular safety hazard criterion based at least on an outcome of the analysis. For example, in embodiment 500 shown in FIG. 5, an analysis component 312 can generate the condition metric and can supply such condition to a hazard response component 510 that can ascertain that the condition satisfies the vehicular hazard criterion. In addition or in the alternative, the communication platform 214 can acquire (e.g., receive wirelessly) the condition metric from an external source, such as another vehicle or infrastructure, and can supply the condition metric to the hazard response component 510 for analysis thereof. In certain implementations, the vehicular safety hazard criterion can be embodied in or can include a frequency of swerving that is above a predetermined threshold; an inter-vehicle distance below recommended safety guidelines (e.g., 10 meters per 10 Km/h in vehicle speed) that is sustained for a predetermined period; elevated frequency (e.g., frequency above a threshold) of switching between periods of acceleration and deceleration; speed significantly above the speed limit; a combination thereof; or the like. One or more vehicular safety hazard criteria can be retained in hazard assessment storage 540 within the repository 218 or any other repository or memory device functionally coupled to the ES assessment component 310.

In a scenario in which the ES assessment platform 120 ascertains—via, for example, the hazard response component 510—that a safety hazard criterion is satisfied, the ES assessment platform 120 can configure a vehicle component to operate within certain bounds or specifications that can permit the adjustment of the emotional state of the operator. To at least such end, in one aspect, a component that ascertains fulfillment of the hazard criterion (for example, the hazard response component 510) can transmit configuration instruction(s) to the vehicle component. The configuration instruction(s) can be transmitted in a format suitable for communication with the vehicle component. The format can be dictated by a packet-switched protocol for communication or a circuit-switched protocol for communication. The vehicle component can be included in a group of vehicle components that can be configured to attain certain performance and/or operational condition of the vehicle. For instance, in embodiment 500, the group of vehicle components can include the rendering unit(s) 230, the control component(s) 520, and the lighting component(s) 530. As illustrated, at least one of the control component(s) 520 can be functionally coupled to the communication platform 214 via one or more links 524, and at least one of the lighting component(s) 530 can be functionally coupled to the communication platform 214 via one or more links 534.

In certain embodiments, the vehicle component can include a content rendering unit (such as a display unit or a display terminal, a loudspeaker, or the like) which can be included in the rendering unit(s) 230; an in-cabin ambient control unit (e.g., a lighting fixture, a temperature control unit, a seat-firmness unit, or the like); or an operation control unit (e.g., a throttle or an engine control unit functionally coupled thereto). The in-cabin ambient control unit can be included in one of the control component(s) 520 or the lighting component(s) 530. In certain implementations, for example, the ES assessment platform 120 can configure a sound system to render music (e.g., to playback a recording or reproduce stream content from a radio station) or to playback recorded messages in order to modify the behavior of the operator of the vehicle in response to ascertaining that the safety hazard criterion is satisfied. Similarly, the ES assessment platform 120 can configure an air-conditioning component to lower the temperature of the vehicle's cabin and thus adjust the emotional state of the operator. For another example, the ES assessment platform 120 can actuate an artificial intelligence (AI) component configured to recognize speech and, in response, to provide autonomous aural responses, and can configure the sound system or a portion thereof to collect ambient sounds and deliver responses from the AI component. In such example, a conversation can be established between the AI component and the operator of the vehicle, and the emotional state may be adjusted to anonhazardous condition. In certain implementations, such AI component can be embodied or can comprise the feature extraction component 334.

Figure 3C:
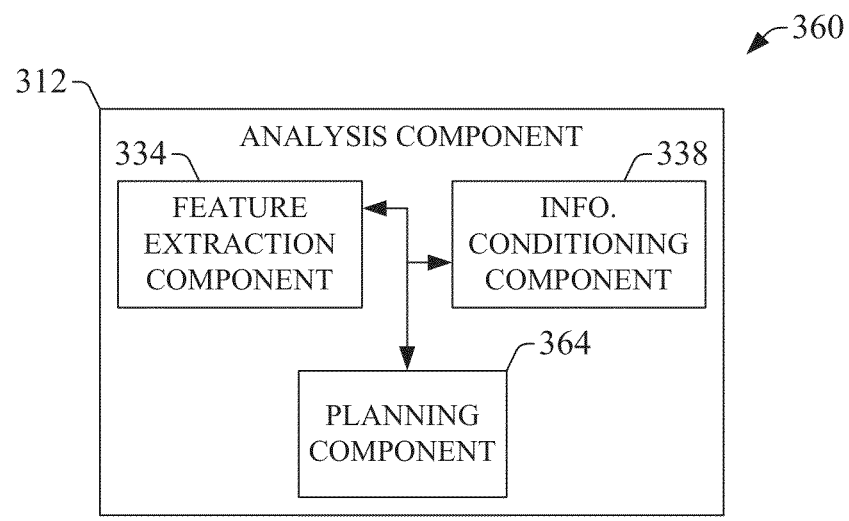
Figure 4:
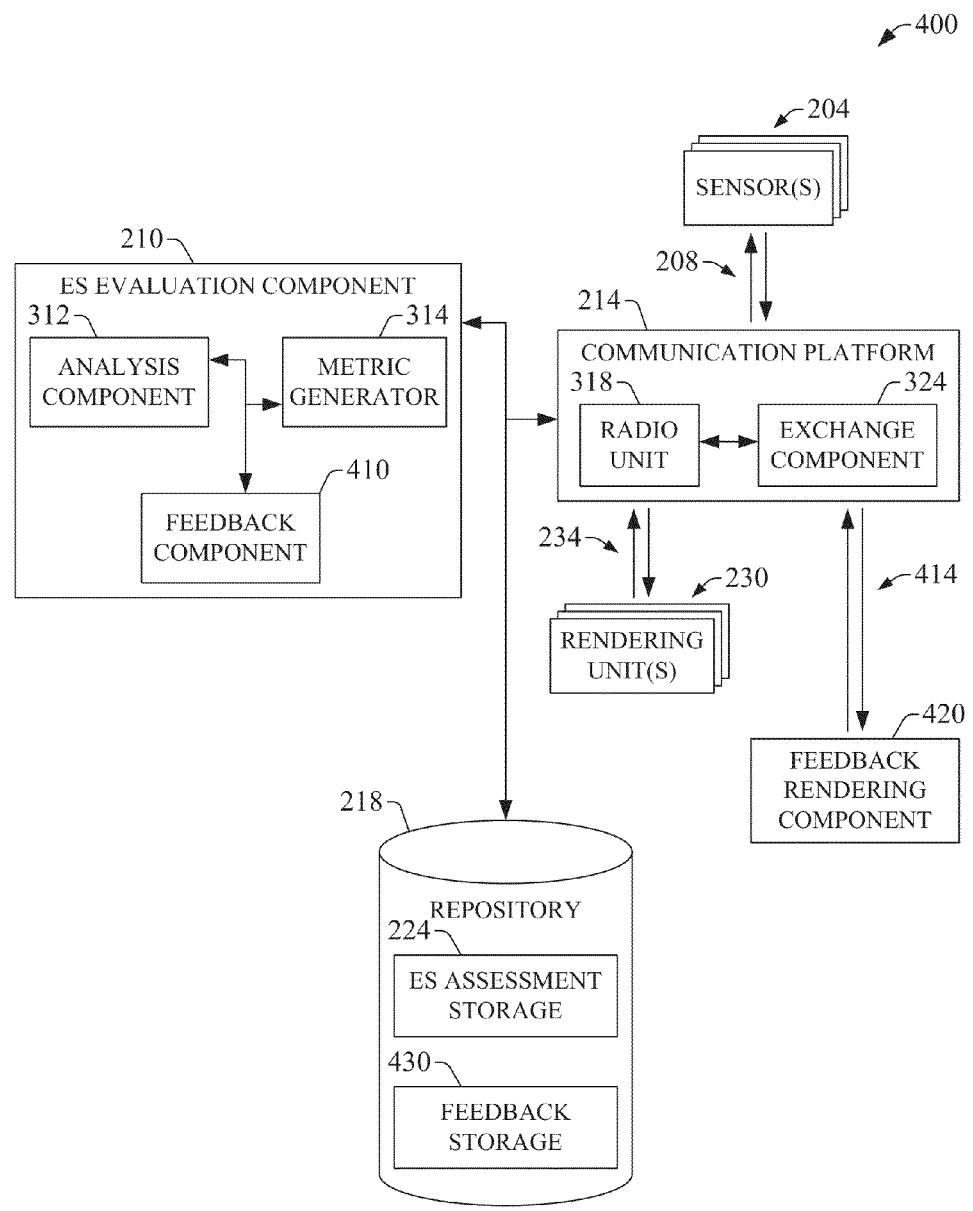
FIGS. 4-5 illustrate other example systems in accordance with one or more aspects of the disclosure.

In certain embodiments, the ES assessment platform 120 can generate information indicative of a satisfactory route (also referred to as generating a route) between an origin and a destination in order to improve a condition metric of a vehicle that satisfies a vehicular safety hazard condition. The satisfactory route can be an optimal route, a nearly-optimal route, or a route having a specific quality (e.g., second best route, third best route, and the like), and can include specific landscapes or specific types of roads (e.g., countryside roads, back roads, surface roads, or the like) that may be conducive to a more relaxed operation of the vehicle. The satisfactory road can be a previously traveled road that has a record of yielding satisfactory emotional conditions of the operators of the vehicles that have traveled such road. In one of such embodiment, the ES assessment platform 120 can include a component (e.g., the analysis component 312) that can generate information indicative of a satisfactory route. To at least such end, in certain implementations, such as embodiment 360 illustrated in FIG. 3C, the component (e.g., analysis component 312) that can generate such a route can include another component, such as planning component 364, that can generate information indicative of the satisfactory route.

In one or more embodiments, management of the emotional state of an operator or an occupant of a vehicle can be implemented proactively. The ES assessment platform 120 can determine (e.g., compute, acquire, or the like) a travel time for a route between an origin and a destination, and can utilize or otherwise leverage the travel time to provide a recommendation for content that is configured to render within substantially the travel time and to adjust the emotional state of the operator of the vehicle or an occupant thereof to a satisfactory state. Rendering the recommended content during the course of operating the vehicle in the route may yield a satisfactory emotional condition of the operator or occupant of the vehicle. It should be appreciated that such route can be a satisfactory route as described herein. In certain embodiments, the planning component 364 can determine the travel time. In addition or in the alternative, the planning component 364 can generate the recommendation for content as described herein based at least in part on the travel time that is determined.

FIGS. 6-9 illustrate block diagrams of example operational environments for context-rich communication between a vehicle and a device in accordance with one or more aspects of the disclosure. These example operational environments are only illustrative and are not intended to suggest or otherwise convey any limitation as to the scope of use or functionality of the operating environments' architecture. In addition, the operational environments should not be interpreted as having any dependency or requirement relating to any one or combination of components illustrated in these example operational environments. These operational environments can embody or can comprise the ES assessment platform 120, the ES assessment platform 120 and another ES assessment platform in another vehicle, or the like.

The operational environment 600 represents an example software implementation of the various aspects or features of the disclosure in which the processing or execution of operations described in connection with assessment and management of an emotional state of a vehicle operator can be performed in response to execution of one or more software components at the computing device 610. It should be appreciated that the one or more software components can render the computing device 610, or any other computing device that contains such components, a particular machine for assessment and/or management of a vehicle operator as described herein, among other functional purposes. A software component can be embodied in or can comprise one or more computer-accessible instructions, e.g., computer-readable and/or computer-executable instructions. In one scenario, at least a portion of the computer-accessible instructions can embody one or more of the example methods presented in FIGS. 10-11 and various call flows described herein. For instance, to embody one such method, at least the portion of the computer-accessible instructions can be persisted (e.g., stored, made available, or stored and made available) in a computer storage non-transitory medium and executed by a processor. The one or more computer-accessible instructions that embody a software component can be assembled into one or more program modules, for example, that can be compiled, linked, and/or executed at the computing device 610 or other computing devices. Generally, such program modules comprise computer code, routines, programs, objects, components, information structures (e.g., data structures and/or metadata structures), etc., that can perform particular tasks (e.g., one or more operations) in response to execution by one or more processors, which can be integrated into the computing device 610 or functionally coupled thereto.

The various example embodiments of the disclosure can be operational with numerous general purpose or special purpose computing system environments or configurations. Examples of well-known computing systems, environments, and/or configurations that can be suitable for implementation of various aspects or features of the disclosure in connection with the assessment and/or management of an emotional state of a vehicle operator can comprise personal computers; server computers; laptop devices; handheld computing devices, such as mobile tablets; wearable computing devices; and multiprocessor systems. Additional examples can include set-top boxes, programmable consumer electronics, network personal computers (PCs), minicomputers, mainframe computers, blade computers, programmable logic controllers, distributed computing environments that comprise any of the above systems or devices, and the like.

As illustrated, the computing device 610 can comprise one or more processors 612, a radio unit 614, one or more input/output (I/O) interfaces 616, a memory 630, and a bus architecture 632 (also termed bus 632) that functionally couples various functional elements of the computing device 610. The bus 632 can include at least one of a system bus, a memory bus, an address bus, or a message bus, and can permit the exchange of information (data, metadata, and/or signaling) between the processor(s) 612, the I/O interface(s) 616, and/or the memory 630, or any respective functional element therein. In certain scenarios, the bus 632 in conjunction with one or more internal programming interfaces 650 (also referred to as interface(s) 650) can permit such exchange of information. The internal programming interfaces 650 can embody one or more application programming interfaces (APIs) and, in response to execution by a processor, can permit the exchange of information between different portions of the one or more ES assessment and management component(s) 636. In scenarios in which processor(s) 612 include multiple processors, the computing device 610 can utilize parallel computing.

The I/O interface(s) 616 permit communication of information between the computing device and an external device. As an example, the external device can be embodied in or can comprise a sensor of the sensor(s) 204. As another example, the external device can be embodied in or can comprise another computing device, such as a network element (e.g., a service component of the service component(s) 244) or an end-user device. Such communication can include direct communication or indirect communication, such as exchange of information between the computing device 610 and the external device via a network or elements thereof. As illustrated, the I/O interface(s) 616 can comprise one or more of network adapter(s) 618, peripheral adapter(s) 622, and rendering unit(s) 626. Such adapter(s) can permit or facilitate connectivity between the external device and one or more of the processor(s) 612 or the memory 630. In one aspect, at least one of the network adapter(s) 618 can couple functionally the computing device 610 to one or more devices 670 via one or more traffic and signaling pipes 660 that can permit or facilitate the exchange of traffic 662 and/or signaling 664 between the computing device 610 and the one or more devices 670. The device(s) contained in the one or more devices 670 can be an electronic component or an electromechanical component having suitable architecture (e.g., circuitry) for a specific functionality (computing, lighting, actuation, sensing, or the like). Such architecture can provide certain respective devices with computing functionality and associated computing resources (e.g., processor(s), memory devices(s), bus structure and related communication bandwidth). For other device(s) contained in the one or more devices 670, the architecture can provide nearly entirely analogic functionality.

Such network coupling provided at least in part by the at least one of the network adapter(s) 618 can be implemented in a wired environment, a wireless environment, or both. The information that is communicated by the at least one network adapter can result from implementation of one or more operations in a method of the disclosure. Such output can be any form of visual representation, including, hut not limited to, textual, graphical, animation, audio, tactile, and the like. In certain embodiments, each of the device(s) 670 can have substantially the same architecture as the computing device 610.

The I/O interface(s) 616 can comprise rendering unit(s) 626 that can include functional elements (e.g., lights, such as light-emitting diodes; a display, such as a liquid crystal display (LCD); combinations thereof, or the like) that can permit control of the operation of the computing device 610, or can permit conveying or revealing operational conditions of the computing device 610.

As described herein, the computing device 610 also includes a radio unit 614 that can permit the computing device 610 to communicate wirelessly with other devices (an IVI system, a meter or other type of monitor component, an RFID unit in a vehicle, or the like). In one embodiment, e.g., example embodiment 700 shown in FIG. 7, the radio unit 614 can comprise one or more antennas 702, a set of one or more transmitters/receivers 706, and components therein (amplifiers, filters, etc.), functionally coupled to a multiplexer/demultiplexer (mux/demux) unit 708, a modulator/demodulator (mod/demod) unit 716 (also referred to as modem 716), and a coder/decoder unit 712 (also referred to as codec 712). Each of the transmitter(s)/receiver(s) 706 can form respective transceiver(s) that can transmit and receive wireless signals (e.g., electromagnetic radiation) via the one or more antennas 702.

Electronic components and associated circuitry, such as mux/demux unit 708, codec 712, and modem 716 can permit or facilitate processing and manipulation, e.g., coding/decoding, deciphering, and/or modulation/demodulation, of signal(s) received by the computing device 610 and signal(s) to be transmitted by such device. In one aspect, received and transmitted wireless signals can be modulated and/or coded, or otherwise processed, in accordance with one or more radio technology protocols (e.g., 3rd Generation Partnership Project (3GPP) Universal Mobile Telecommunication System (UMTS), 3GPP Long Term Evolution (LTE), or the like).

The electronic components in the described radio unit, including the one or more transmitters/receivers 706, can exchange information (e.g., data, metadata, code instructions, signaling and related payload data, combinations thereof, or the like) through a bus 714, which can embody or can comprise at least one of a system bus, an address bus, a data bus, a message bus, a reference link or interface, a combination thereof, or the like. Each of the one or more transmitters/receivers 706 can convert signals from analog to digital and vice versa. In addition or in the alternative, the transmitter(s)/receiver(s) 706 can divide a single data stream into multiple parallel data streams, or perform the reciprocal operation. Such operations may be conducted as part of various multiplexing schemes. As illustrated, the mux/demux unit 708 is functionally coupled to the one or more transmitters/receivers 706 and can permit processing of signals in time and frequency domain. In one aspect, the mux/demux unit 708 can multiplex and demultiplex information (e.g., data, metadata, and/or signaling) according to various multiplexing schemes such as time division multiplexing (TDM), frequency division multiplexing (FDM), orthogonal frequency division multiplexing (OFDM), code division multiplexing (CDM), or space division multiplexing (SDM). In addition or in the alternative, in another aspect, the mux/demux unit 708 can scramble and spread information (e.g., codes) according to almost any code, such as Hadamard-Walsh codes, Baker codes, Kasami codes, polyphase codes, and the like. The modem 716 can modulate and demodulate information (e.g., data, metadata, signaling, or a combination thereof) according to various modulation techniques, such as frequency modulation (e.g., frequency-shift keying), amplitude modulation (e.g., M-ary quadrature amplitude modulation (QAM), with M a positive integer; amplitude-shift keying (ASK)), phase-shift keying (PSK), and the like). In addition, the processor(s) 612 can permit the computing device 610 to process data (e.g., symbols, bits, or chips) for multiplexing/demultiplexing, modulation/demodulation (such as implementing direct and inverse fast Fourier transforms) selection of modulation rates, selection of data packet formats, inter-packet times, and the like.

The codec 712 can operate on information (e.g., data, metadata, signaling, or a combination thereof) in accordance with one or more coding/decoding schemes suitable for communication, at least in part, through the one or more transceivers formed from respective transmitter(s)/receiver(s) 706. In one aspect, such coding/decoding schemes, or related (procedure(s), can be retained as a group of one or more computer-accessible instructions (computer-readable instructions, computer-executable instructions, or a combination thereof) in memory 630. In a scenario in which wireless communication between the computing device 610 and another device (e.g., a device of the device(s) 670) utilizes multiple-input multiple-output (MIMO), multiple-input single-output (MISO), single-input multiple-output (SIMO) or single-input single-output (SISO) operation, the codec 712 can implement at least one of space-time block coding (STBC) and associated decoding, or space-frequency block coding (SFBC) and associated decoding. In addition or in the alternative, the codec 712 can extract information from data streams coded in accordance with spatial multiplexing schemes. In one aspect, to decode received information (e.g., data, metadata, signaling, or a combination thereof), the codec 712 can implement at least one of computation of log-likelihood ratios (LLR) associated with constellation realization for a specific demodulation; maximal ratio combining (MRC) filtering; maximum-likelihood (ML) detection; successive interference cancellation (SIC) detection; zero forcing (ZF) and minimum mean square error estimation (MMSE) detection; or the like. The codec 712 can utilize, at least in part, mux/demux unit 708 and mod/demod unit 716 to operate in accordance with aspects described herein.

The computing device 610 can operate in a variety of wireless environments having wireless signals conveyed in different electromagnetic radiation (EM) frequency bands. To at least such end, the radio unit 614 can process (code, decode, format, etc.) wireless signals within a set of one or more EM frequency bands (also referred to as frequency bands) comprising one or more of radio frequency (RF) portions of the EM spectrum, microwave portion(s) of the EM spectrum, or infrared (IR) portion of the EM spectrum. In one aspect, the set of one or more frequency bands can include at least one of (i) all or most licensed EM frequency bands, or (ii) all or most unlicensed frequency bands currently available for telecommunication.

In the example embodiment 700, in certain implementations, one or more of the mux/demux unit 708, the modem 716, or the codec 712 can utilize or otherwise leverage at least one of the processor(s) to implement the communication processing functionality described herein. In one aspect, the at least one processor can execute one or more computer-accessible instructions retained in memory 630 in order to implement the communication processing functionality. In addition, in connection with at least wireless communication, the memory 630 or a memory element therein, such the functionality instructions storage 646 can be embodied in or can comprise a removable element, such as a subscriber identification module (SIM) card storage, a universal integrated circuit card (UICC) storage, or a removable user identity module (RUIM).

The computing device 610 also can include the bus 632, which represents one or more of several possible types of bus structures, including a memory bus or memory controller, a peripheral bus, an accelerated graphics port, and a processor or local bus using any of a variety of bus architectures. As an illustration, such architectures can comprise an Industry Standard Architecture (ISA) bus, a Micro Channel Architecture (MCA) bus, an Enhanced ISA (EISA) bus, a Video Electronics Standards Association (VESA) local bus, an Accelerated Graphics Port (AGP) bus, a Peripheral Component Interconnects (PCI) bus, a PCI-Express bus, a Personal Computer Memory Card Industry Association (PCMCIA) bus, a Universal Serial Bus (USB) and the like. The bus 632, and all buses described herein can be implemented over a wired or wireless network connection and each of the subsystems, including the processor(s) 612, the memory 630 and memory elements therein, and the I/O interface(s) 616 can be contained within one or more remote computing devices 670 at physically separate locations, connected through buses of this form, in effect implementing a fully distributed system.

The computing device 610 can comprise a variety of computer-readable media. Computer-readable media can be any available media—transitory and non-transitory—that can be accessed by a computing device. In one aspect, computer-readable media can comprise computer non-transitory storage media (or computer-readable non-transitory storage media) and communications media. Example computer-readable non-transitory storage media can be any available media that can be accessed by the computing device 610, and can comprise, for example, both volatile and non-volatile media, and removable and/or non-removable media. In one aspect, the memory 630 can comprise computer-readable media in the form of volatile memory, such as random access memory (RAM), and/or non-volatile memory, such as read-only memory (ROM).

The memory 630 can comprise functionality instructions storage 634 and functionality information storage 638. The functionality instructions storage 634 can comprise computer-accessible instructions that, in response to execution (by at least one of the processor(s) 612), can implement one or more of the functionalities of the disclosure. The computer-accessible instructions can embody or can comprise one or more software components illustrated as ES assessment and management component(s) 636. In one scenario, execution of at least one component of the ES assessment and management component(s) 636 can implement one or more of the example methods 1000 through 1100. For instance, such execution can cause a processor that executes the at least one component to carry out a disclosed example method. It should be appreciated that, in one aspect, a processor of the processor(s) 612 that executes at least one of the ES assessment and management component 636 can retrieve information from or retain information in the ES assessment and management information 640 in the functionality information storage 638 in order to operate in accordance with the functionality programmed or otherwise configured by the ES assessment and management component(s) 636. Such information can include at least one of code instructions, information structures, or the like. At least one of the one or more interfaces 650 (e.g., application programming interface(s)) can permit or facilitate communication of information between two or more components within the functionality instructions storage 634. The information that is communicated by the at least one interface can result from implementation of one or more operations in a method of the disclosure. In certain embodiments, one or more of the functionality instructions storage 634 and the functionality information storage 638 can be embodied in or can comprise removable/non-removable, and/or volatile/non-volatile computer storage media.

At least a portion of at least one of the ES assessment and management component(s) 636 or the ES assessment and management information 640 can program or otherwise configure one or more of the processors 612 to operate at least in accordance with the functionality described herein. In one embodiment, e.g., example embodiment 800 in FIG. 8, the ES assessment and management component(s) 636 contained in the functionality instruction(s) storage 634 can include the exchange component 324, and the ES evaluation component 210 and components therein, e.g., the analysis component 312 and the metric generator 314. In another embodiment, the ES assessment and management component(s) 636 can include the exchange component 324, the ES evaluation component 210 and one or more ES management component(s), such as the feedback component 410 or the hazard response component 510. It should be recognized that in such embodiment, hardware or firmware functional elements of the exchange component 324 can be embodied in suitable components of the computing device 610. In addition, in example embodiment 800, the functionality information storage 638 can comprise the ES assessment storage 224. One or more of the processor(s) 612 can execute at least one of such components and utilize or otherwise leverage at least a portion of the information in the functionality information storage 638 in order to assess or manage, or both assess and manage, an emotional state of an operator of a vehicle in accordance with one or more aspects described herein.

It should be appreciated that, in certain scenarios, the functionality instruction(s) storage 634 can embody or can comprise a computer-readable non-transitory storage medium having computer-accessible instructions that, in response to execution, cause at least one processor (e.g., one or more of processor(s) 612) to perform a group of operations comprising the operations or blocks described in connection with the disclosed methods.

In addition, the memory 630 can comprise computer-accessible instructions and information (e.g., data and/or metadata) that permit or facilitate the operation and/or administration (e.g., upgrades, software installation, any other configuration, or the like) of the computing device 610. Accordingly, as illustrated, the memory 630 can comprise a memory element 642 (labeled operating system (OS) instruction(s) 642) that contains one or more program modules that embody or include one or more operating systems, such as Windows operating system, Unix, Linux, Symbian, Android, Chromium, and substantially any operating system suitable for mobile computing devices or tethered computing devices. In one aspect, the operational and/or architectural complexity of the computing device 610 can dictate a suitable operating system. The memory 630 also comprises a system information storage 646 having data and/or metadata that permits or facilitate operation and/or administration of the computing device 610. Elements of the OS instruction(s) 642 and the system information storage 646 can be accessible or can be operated on by at least one of the processor(s) 612.

It should be recognized that while the functionality instructions storage 634 and other executable program components, such as the OS instruction(s) 642, are illustrated herein as discrete blocks, such software components can reside at various times in different memory components of the computing device 610, and can be executed by at least one of the processor(s) 612. In certain scenarios, an implementation of the ES assessment and management component(s) 636 can be retained on or transmitted across some form of computer-readable media.

The computing device 610 and/or one of the device(s) 670 can include a power supply (not shown), which can power up components or functional elements within such devices. The power supply can be a rechargeable power supply, e.g., a rechargeable battery, and it can include one or more transformers to achieve a power level suitable for operation of the computing device 610 and/or one of the device(s) 670, and components, functional elements, and related circuitry therein. In certain scenarios, the power supply can be attached to a conventional power grid to recharge and ensure that such devices can be operational. In one aspect, the power supply can include an I/O interface (e.g., one of the network adapter(s) 618) to connect operationally to the conventional power grid. In another aspect, the power supply can include an energy conversion component, such as a solar panel, to provide additional or alternative power resources or autonomy for the computing device 610 and/or one of the device(s) 670.

As described herein, the computing device 610 can operate in a networked environment by utilizing connections to one or more devices 670 which can be remotely located. As an illustration, a remote device can be a personal computer, a portable computer, a server, a router, a network computer, a peer device or other common network node, a sensor, a control component, an actuator, a transducer, a lighting fixture, a terminal display or any other display unit, any combination of the foregoing, and so on. As described herein, connections (physical and/or logical) between the computing device 610 and a device of the one or more remote devices 670 can be made via one or more traffic and signaling pipes 660, which can comprise wireline link(s) and/or wireless link(s) and several network elements (such as routers or switches, concentrators, servers, and the like) that form a local area network (LAN) and/or a wide area network (WAN). Such networking environments generally are conventional and commonplace in dwellings, offices, enterprise-wide computer networks, intranets, local area networks, and wide area networks.

Figure 9:
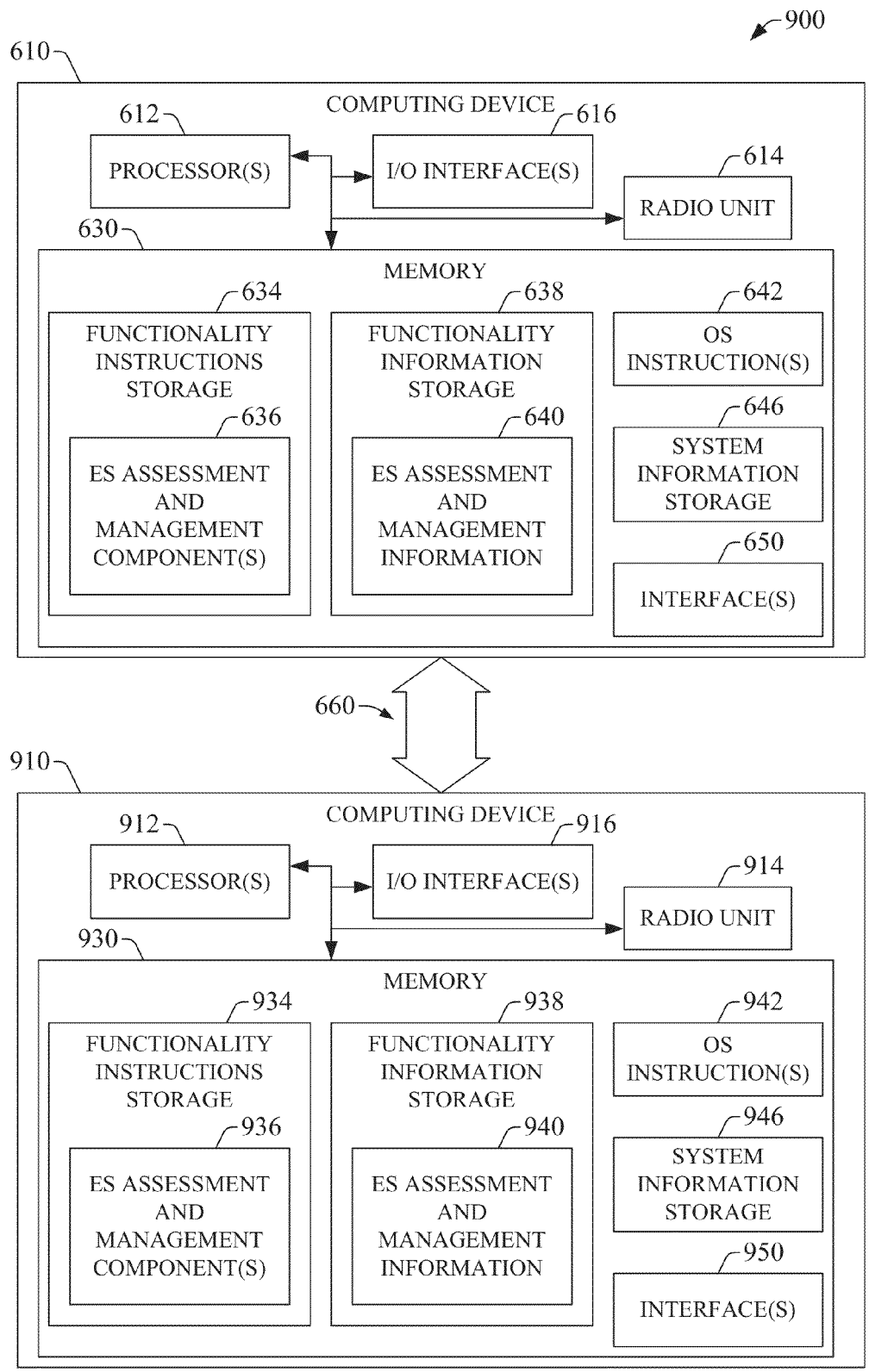

In one or more embodiments, such as example embodiment 900 shown in FIG. 9, one or more of the disclosed methods, for example, can be practiced in distributed computing environments (e.g., grid-based environments) where tasks can be performed by remote processing devices (at least one of device(s) 670) that are functionally coupled (e.g., communicatively linked or otherwise coupled) through a network having traffic and signaling pipes and related network elements. In a distributed computing environment, in one aspect, one or more software components (such as program modules) can be located in both a local computing device 610 and at least one remote computing device, such as computing device 910. As illustrated and described herein, the at least one remote computing device, e.g., computing device 910, can have substantially the same architecture and associated functionality as the computing device 610. For instance, the computing device 910 can comprise processor(s) 912, a radio unit 914, I/O interface(s) 916, and a memory 930, where a bus architecture can couple functionally two or more of such elements. The memory 930 can comprise a functionality instructions storage 934 having one or more ES assessment and management component(s) 936, and a functionality information storage 938 having ES assessment and management information 940. The memory 930 also can comprise OS instruction(s) 942 and system information storage 946 that can permit, at least in part, operation and/or administration of the computing device 910. One or more internal programming interfaces 950 (represented as interface(s) 950 in FIG. 9) can permit or facilitate the exchange of information between the ES assessment and management component(s) 936 and the functionality information storage 938. In a scenario in which several components are present in the group of ES assessment and management component(s) 936, at least one interface of the interface(s) 950 can permit or facilitate exchange of information between at least two of such components.

In one implementation, the computing device 610 can embody or can comprise the exchange component 324 and a portion of the subcomponents of the ES evaluation component 210, whereas the computing device 910 can comprise or can embody another portion of the ES evaluation component 210. Other distributions of the exchange component 324 and portions of the ES evaluation component 210 are contemplated and can be implemented. Similarly, the ES assessment storage 224 and the ES management storage 810, which can comprise one or more of the feedback storage 430 or the hazard response storage 540 also can be distributed between the computing device 610 and the computing device 910 or other devices (such as dedicated storage or memory devices).

Figure 10:
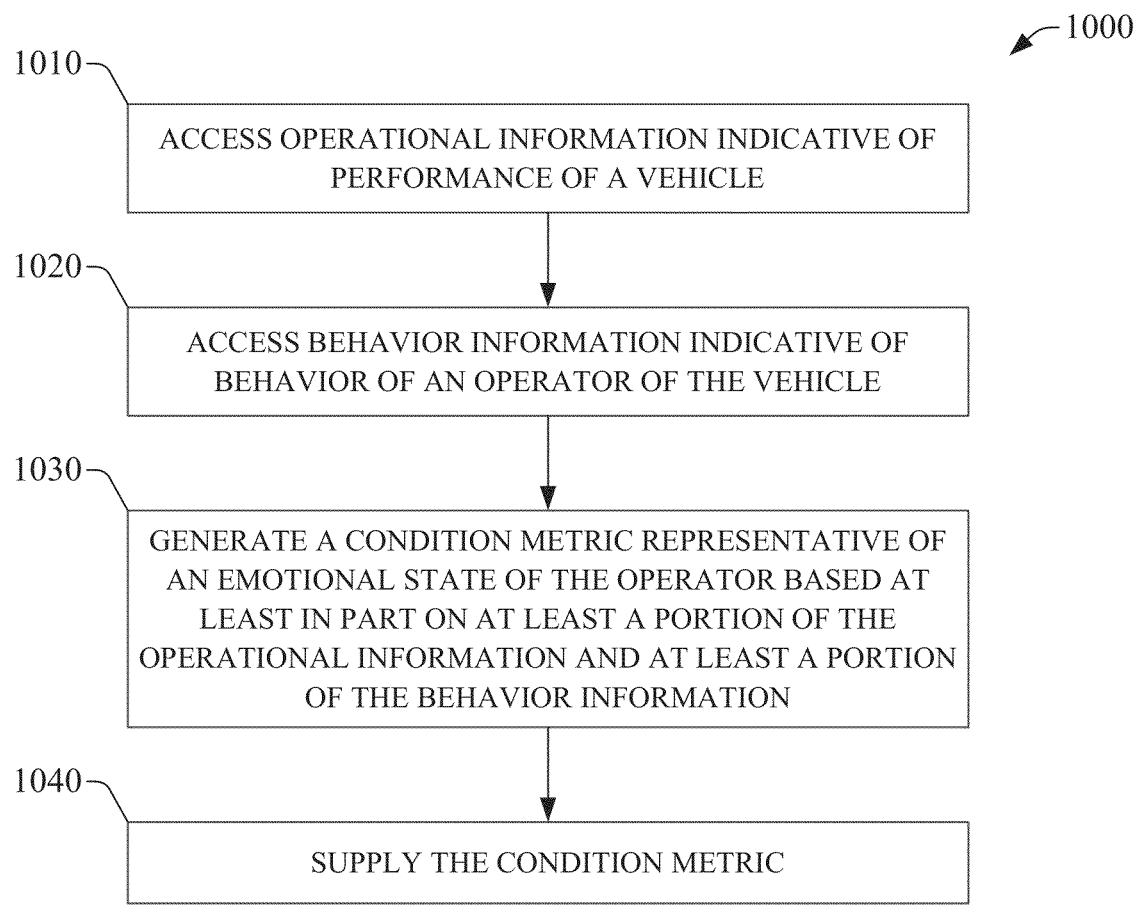
FIGS. 10-11 illustrate example methods in accordance with one or more aspects of the disclosure.
Figure 11:
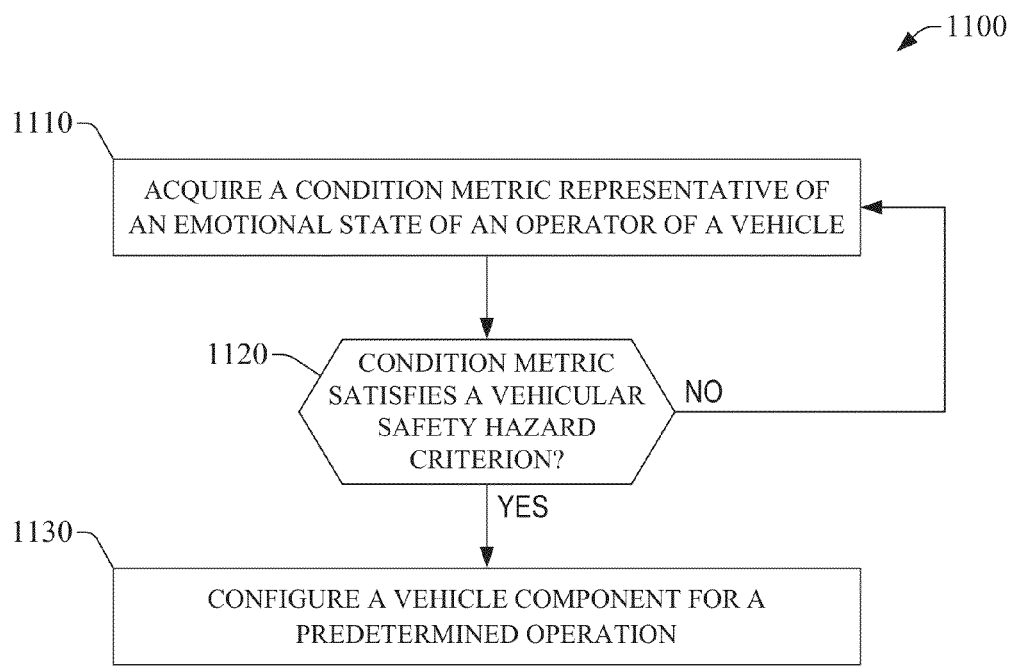

In view of the aspects described herein, example methods that can be implemented in accordance with the disclosure can be better appreciated with reference to the flowcharts in FIGS. 10-11. For purposes of simplicity of explanation, the example methods disclosed herein are presented and described as a series of blocks (with each block representing an action or an operation in a method, for example). However, it is to be understood and appreciated that the disclosed methods are not limited by the order of blocks and associated actions or operations, as some blocks may occur in different orders and/or concurrently with other blocks from that shown and described herein. For example, the various methods or processes of the disclosure can be alternatively represented as a series of interrelated states or events, such as in a state diagram. Furthermore, not all illustrated blocks, and associated action(s), may be required to implement a method in accordance with one or more aspects of the disclosure. Further yet, two or more of the disclosed methods or processes can be implemented in combination with each other, to accomplish one or more features or advantages described herein.

It should be appreciated that the methods of the disclosure can be retained on an article of manufacture, or computer-readable storage medium, to permit or facilitate transporting and transferring such methods to a computing device (e.g., a desktop computer; a mobile computer, such as a tablet computer or a smartphone; a gaming console, a mobile telephone; a blade computer; a programmable logic controller, and the like) for execution, and thus implementation, by a processor of the computing device or for storage in a memory thereof or functionally coupled thereto. In one aspect, one or more processors, such as processor(s) that implement (e.g., execute) one or more of the disclosed methods, can be employed to execute code instructions retained in a memory, or any computer- or machine-readable medium, to implement the one or more methods. The code instructions can provide a computer-executable or machine-executable framework to implement the methods described herein.

FIG. 10 illustrates a flowchart of an example method 1000 for assessing an emotional state of an operator of a vehicle in accordance with at least certain aspects of the disclosure. One or more computing devices having at least one processor or being functionally coupled to at least one processor can implement (e.g., compile, execute, compile and execute, etc.) one or more blocks of the subject example method 1000. In other scenarios, one or more blocks of the example method 1000 can be implemented in a distributed fashion by two or more computing devices contained in a system. Each of the two or more computing devices can have at least one processor or can be functionally coupled to at least one processor, where such processor(s) can implement at least one of the one or more blocks.

At block 1010, operational information indicative of performance of the vehicle (e.g., vehicle 104) is accessed. As described herein, accessing the operational information can comprise receiving at least a portion of the operational information from one or more sensors (e.g., sensor(s) 204) of a plurality of sensors. It should be appreciated that in certain scenarios, each sensor of the plurality of sensors can detect or can be configured to detect motion of the vehicle, whereas in other scenarios a portion of the plurality of sensors can detect or can be configured to detect the motion of the vehicle.

At block 1020, behavioral information indicative of behavior of an operator of the vehicle is accessed (e.g., received, retrieved, or the like). In one aspect, accessing the behavioral information can comprise accessing imaging information indicative of an appearance of the operator of the vehicle. As described herein, in one aspect, such information (e.g., data, metadata, and/or signaling) can be received from one or more cameras, such as operator-facing cameras, that generate the imaging information. In another aspect, the imaging information that is received can be analyzed or otherwise processed in order to generate, and thus access, at least a portion of the behavioral information. Generating at least the portion of the behavioral information can include extracting specific features from the imaging information. For instance, one or more facial features can be extracted from the imaging information. Accordingly, in one aspect, accessing the behavioral information can comprise determining a facial feature of the operator of the vehicle based at least in part on the imaging information. To determine the facial feature, in one aspect, the computing device or processor(s) functionally coupled thereto that implements the subject example method can implement at least a facial recognition technique. It should be appreciated that other feature extraction technique(s) can be implemented in addition or in the alternative to the facial recognition technique.

In addition or in the alternative, accessing the behavioral information can comprise accessing audio information indicative of a speech segment uttered by the operator of the vehicle. Such information can be generated by a microphone that is available (e.g., installed and properly functional) within the cabin of the vehicle. In another aspect, the audio information can be analyzed or otherwise processed e.g., audio noise can be removed or mitigated from the audio information) in order to generate, and thus access, at least a portion of the behavioral information. Generating at least the portion of the behavioral information can include determining a verbal feature of the segment speech based at least in part on the audio information. As described herein, in one aspect, the verbal feature can be representative of the emotional state of the operator.

Moreover or as another alternative, accessing the behavioral information can comprise accessing gesture information indicative of movement of the operator of the vehicle. The gesture information can be generated, at least in part, by a camera of the one or more cameras that can generate the imaging information described herein, and/or a gesture-sensitive device (e.g., a touch screen or touch surface). In certain implementations, accessing the behavioral information can comprise determining a gesture of the operator of the vehicle based at least in part on the gesture information.

In certain embodiments, in addition or as an alternative, wellness information indicative of a physical condition of the operator of the vehicle can be accessed. As described herein, the physical condition can include vitals for the operator of the vehicle, such as blood pressure, blood sugar concentration, heartbeat rate, a combination of the foregoing, or the like.

At block 1030, a condition metric representative of an emotional state of the operator is generated based at least in part on at least a portion of the operational information and at least a portion of the behavioral information. The block 1030 can be referred to as a generating operation and, in one aspect, can comprise integrating at least the portion of the operational information and at least the portion of the behavioral information into vehicular context information that can permit generating the emotional state in accordance with aspects described herein. In certain embodiments, the generating operation can comprise inferring the emotional state via, at least in part, AI techniques applied to at least a portion of the vehicular context information. In addition, the generating operation can comprise mapping the inferred emotional state into a category within a predetermined classification of emotional states. The condition metric can be generated by assigning a specific metric (numeric or otherwise) to the category.

At block 1040, the condition metric is supplied. Block 1040 can be referred to as a supplying operation and, in one aspect, can comprise rendering the condition metric. In one implementation, for example, the rendering can comprise providing at least one of a visual representation of the condition metric, an aural representation of the condition metric, or a haptic representation of the condition metric. In another implementation, for example, the rendering can comprise rendering the condition metric at a predetermined exterior area of the vehicle. As described herein, the exterior area can comprise one or more display units (e.g., display units 130) mounted or otherwise attached to a specific portion of the vehicle. In yet another implementation, the rendering can comprise rendering the condition metric at a predetermined interior area of the vehicle in accordance with the visual representation, the aural representation, and/or the haptic representation.

In certain implementations, the supplying operation can comprise transmitting the condition metric to other vehicle (e.g. vehicle 150). In one aspect, the condition metric can be transmitted wirelessly. In another aspect, the condition metric can be transmitted via a link tethered to the other vehicle. Similarly, yet not identically, the supplying operation can comprise supplying the information to infrastructure (e.g., an access point, which can be located within a tower or a billboard; a toll booth; or the like) within an environment of the vehicle.

In certain embodiments, the example method 1000 can comprise receiving at least one condition metric from at least one other vehicle. The at least one condition metric can be received at the computing device that implements the subject example method 1000 or at a component thereof (such as a processor, a platform, or the like). Each condition metric of the at least condition metric can be representative of an emotional state of an operator of a respective vehicle of the at least one other vehicle. In addition, in such embodiments, the example method 1000 can comprise rendering the at least one condition metric at the computing system.

In other embodiments, the example method 1000 can comprise receiving a plurality of condition metrics from a plurality of vehicles. As described herein, each condition metric of the plurality of condition metrics can be representative of an emotional state of an operator of a respective vehicle of the plurality of vehicles. In addition, in such embodiments, the example method can comprise rendering the plurality of condition metrics at the computing system, wherein the plurality of condition metrics can represent a collective emotional state of a plurality of respective operators of the plurality of vehicles. The plurality of condition metrics can be rendered in various manners. For example, the rendering can comprise displaying the plurality of condition metrics in conjunction with a visual representation of a traffic condition, such as a traffic map.

FIG. 11 illustrates a flowchart of an example method 1100 for managing an emotional state of an operator of a vehicle in accordance with at least certain aspects of the disclosure. A computing device or a processor that can implement at least a portion of the example method 1000 also can implement one or more blocks of the subject example method 1100. At block 1110, a condition metric representative of an emotional state of an operator of a vehicle can be acquired (e.g., received, decoded, received and decoded, or the like). At block 1120, it is determined if the condition metric satisfies a vehicular safety hazard criterion. As described herein, such criterion can be embodied in or can include a frequency of swerving that is above a predetermined threshold; an inter-vehicle distance below recommended safety guidelines (e.g., 10 meters per 10 Km/h in vehicle velocity) that is sustained for a predetermined period; elevated frequency (e.g., frequency above a threshold) of switching between periods of acceleration and deceleration; sustained speed significantly above a speed limit; a combination thereof; or the like. In the negative case, flow is directed to block 1110. Yet, in a scenario in which it is ascertained that the safety hazard criterion is satisfied, the method flow is directed to block 1130, at which a vehicle component is configured for a predetermined operation. It should be appreciated that, in one aspect, the vehicle component can be included in a group of vehicle components that are configured to attain certain performance and/or operational condition of the vehicle that can be designed to adjust the emotional state of the operator. As described herein, in one aspect, the vehicle component can include a content rendering unit (such as display unit or a display terminal, an in-cabin ambient control unit (e.g., a lighting fixture, a temperature control unit, a seat-firmness unit, or the like), or an operation control unit.

In one embodiment, the example method 1100 can comprise generating information indicative of a route (also referred to as generating a route) between an origin and a destination, wherein the route is designed to improve the condition metric that satisfies the vehicular safety hazard condition. A satisfactory route can be an optimal route, a nearly-optimal route, or a route having a specific quality (e.g., second best route, third best route, and the like). Generation of such a route can be implemented in addition or as an alternative to implementing block 1130. For instance, for less severe safety hazards posed by the emotional state of the operator of a vehicle, generating such route can be a response to ascertaining that the condition metric satisfies a vehicular hazard condition.

It should be appreciated that, in certain scenarios, the example methods 1000 and 1100 can be combined to form another example method or technique of the disclosure.

In one or more embodiments, management of the emotional state of an operator or an occupant of the vehicle can be implemented proactively by leveraging a planning component (e.g., planning component 364) integrated into or functionally coupled to the computing device or processor that implements the subject example method 1000. In one embodiment, the example method 1000 can include determining a travel time for a route between an origin and a destination. The travel time that is determined can be utilized for providing a recommendation for content that is configured to render within substantially the travel time and to adjust the emotional state of the operator of the vehicle or an occupant thereof to a satisfactory state, thus adjusting the condition metric to a satisfactory level.

Various advantages of the disclosure over conventional technologies for vehicle operator (e.g., driver) safety emerge from the present specification and annexed drawings. One example advantage may be the proactive mitigation of road incidents associated with highly-stressed vehicle operators through communication and customized management of the emotional state of a vehicle operator. By conveying the emotional state of the vehicle operator to other vehicle operators, inter-vehicle awareness of such emotional state can be created. Thus, the likely ensuing action from these operators can be directed to reduce the safety hazard posed by a highly-stressed vehicle operator associated with the communicated emotional state. In connection with the customized management of an emotional state, feedback of the emotional state to the vehicle operator can permit creating intra-vehicle awareness of such state. The likely ensuing action, in one aspect, can be to adjust behavior in order to mitigate, for example, a stress condition, or constrain an excitement condition that may lead to distraction and associated safety risk. Another example advantage of customized management of an emotional state is that specific ambient conditions (e.g., temperature condition, lighting conditions, seat configuration, combination thereof or the like) within the vehicle cabin can be created (e.g., via configuration of certain vehicle components) in response to a specific emotional state of a vehicle operator. In addition, as yet another example advantage, in scenarios in which the emotional state is indicative of a high-stress condition that poses a safety hazard to the vehicle operator, passenger(s) of the vehicle, occupant(s) of other vehicle(s), and/or property, the customized management of such condition can include automated regulation of the vehicle operation in order to achieve, at least substantially, a safe operation condition.

Unless otherwise expressly stated, it is in no way intended that any protocol, procedure, process, or method set forth herein be construed as requiring that its acts or steps be performed in a specific order. Accordingly, where a process or method claim does not actually recite an order to be followed by its acts or steps or it is not otherwise specifically recited in the claims or descriptions of the subject disclosure that the steps are to be limited to a specific order, it is in no way intended that an order be inferred, in any respect. This holds for any possible non-express basis for interpretation, including: matters of logic with respect to arrangement of steps or operational flow; plain meaning derived from grammatical organization or punctuation; the number or type of embodiments described in the specification or annexed drawings, or the like.

As used in this application, the terms "component," "environment," "platform," "system," "architecture," "interface," "unit," "module," and the like are intended to refer to a computer-related entity or an entity related to an operational apparatus with one or more specific functionalities. Such entities may be either hardware, a combination of hardware and software, software, or software in execution. As an example, a component may be, but is not limited to being, a process running on a processor, a processor, an object, an executable portion of software, a thread of execution, a program, and/or a computing device. For example, both a software application executing on a computing device and the computing device can be a component. One or more components may reside within a process and/or thread of execution. A component may be localized on one computing device or distributed between two or more computing devices. As described herein, a component can execute from various computer-readable non-transitory media having various data structures stored thereon. Components can communicate via local and/or remote processes in accordance, for example, with a signal (either analogic or digital) having one or more data packets (e.g., data from one component interacting with another component in a local system, distributed system, and/or across a network such as a wide area network with other systems via the signal). As another example, a component can be an apparatus with specific functionality provided by mechanical parts operated by electric or electronic circuitry that is controlled by a software application or firmware application executed by a processor, wherein the processor can be internal or external to the apparatus and can execute at least a part of the software or firmware application. As yet another example, a component can be an apparatus that provides specific functionality through electronic components without mechanical parts, the electronic components can include a processor therein to execute software or firmware that provides, at least in part, the functionality of the electronic components. An interface can include input/output (I/O) components as well as associated processor, application, and/or other programming components. The terms "component," "environment," "platform," "system," "architecture," "interface," "unit," "module" can be utilized interchangeably and can be referred to collectively as functional elements.

In the present specification and annexed drawings, reference to a "processor" is made. As utilized herein, a processor can refer to any computing processing unit or device comprising single-core processors; single-processors with software multithread execution capability; multi-core processors; multi-core processors with software multithread execution capability; multi-core processors with hardware multithread technology; parallel platforms; and parallel platforms with distributed shared memory. Additionally, a processor can refer to an integrated circuit (IC), an application-specific integrated circuit (ASIC), a digital signal processor (DSP), a field programmable gate array (FPGA), a programmable logic controller (PLC), a complex programmable logic device (CPLD), a discrete gate or transistor logic, discrete hardware components, or any combination thereof designed to perform the functions described herein. A processor can be implemented as a combination of computing processing units. In certain embodiments, processors can utilize nanoscale architectures such as, but not limited to, molecular and quantum-dot based transistors, switches and gates, in order to optimize space usage or enhance performance of user equipment.

In addition, in the present specification and annexed drawings, terms such as "store," storage," "data store," "data storage," "memory," "repository," and substantially any other information storage component relevant to operation and functionality of a component of the disclosure, refer to "memory components;" functional entities embodied in or comprising a memory device or storage device; or components forming the memory device or storage device. It can be appreciated that the memory components or memories described herein embody or comprise non-transitory computer storage media that can be readable or otherwise accessible by a computing device. Such media can be implemented in any methods or technology for storage of information such as computer-readable instructions, information structures, program modules, or other information objects. The memory components or memories can be either volatile memory or non-volatile memory, or can include both volatile and non-volatile memory. In addition, the memory components or memories can be removable or non-removable, and/or internal or external to a computing device or component. Example of various types of non-transitory storage media can comprise hard-disc drives, zip drives, CD-ROM, digital versatile disks (DVD) or other optical storage, magnetic cassettes, magnetic tape, magnetic disk storage or other magnetic storage devices, flash memory cards or other types of memory cards, cartridges, or any other non-transitory medium suitable to retain the desired information and which can be accessed by a computing device.

As an illustration, non-volatile memory can include read only memory (ROM), programmable ROM (PROM), electrically programmable ROM (EPROM), electrically erasable ROM (EEPROM), or flash memory. Volatile memory can include random access memory (RAM), which acts as external cache memory. By way of illustration and not limitation, RAM is available in many forms such as synchronous RAM (SRAM), dynamic RAM (DRAM), synchronous DRAM (SDRAM), double data rate SDRAM (DDR SDRAM), enhanced SDRAM (ESDRAM), Synchlink DRAM (SLDRAM), and direct Rambus RAM (DRRAM). The disclosed memory components or memories of operational environments described herein are intended to comprise one or more of these and/or any other suitable types of memory.

Conditional language, such as, among others, "can," "could," "might," or "may," unless specifically stated otherwise, or otherwise understood within the context as used, is generally intended to convey that certain implementations could include, while other implementations do not include, certain features, elements, and/or operations. Thus, such conditional language generally is not intended to imply that features, elements, and/or operations are in any way required for one or more implementations or that one or more implementations necessarily include logic for deciding, with or without user input or prompting, whether these features, elements, and/or operations are included or are to be performed in any particular implementation.

What has been described herein in the present specification and annexed drawings includes examples of systems, devices, and techniques that can provide assessment and management of an emotional condition of an operator of a vehicle. It is, of course, not possible to describe every conceivable combination of elements and/or methods for purposes of describing the various features of the disclosure, but it can be recognized that many further combinations and permutations of the disclosed features are possible. Accordingly, it may be apparent that various modifications can be made to the disclosure without departing from the scope or spirit thereof. In addition or in the alternative, other embodiments of the disclosure may be apparent from consideration of the specification and annexed drawings, and practice of the disclosure as presented herein. It is intended that the examples put forward in the specification and annexed drawings be considered, in all respects, as illustrative and not restrictive. Although specific terms are employed herein, they are used in a generic and descriptive sense only and not for purposes of limitation.

What is claimed is:

1. A computer-readable non-transitory storage medium encoded with computer-accessible instructions that, in response to execution, cause at least one processor to perform operations for vehicular safety comprising:
   accessing, at a computing system having at least one processor, operational information indicative of performance of a vehicle;
   accessing, at the computing system, behavioral information indicative of behavior of an operator of the vehicle;
   generating, at the computing system, a condition metric representative of an emotional state of the operator based at least in part on at least a portion of the operational information and at least a portion of the behavioral information;
   rendering, by the computing system, the condition metric at a predetermined exterior area of the vehicle;
   determining, by the computing system, a travel time for a route between an origin and a destination;
   providing a recommendation for the route based at least in part on the behavior of the operator, wherein the route is configured to render within substantially the travel time; and
   adjusting the condition metric based on the recommendation.

2. The computer-readable non-transitory storage medium of claim 1, wherein the operations further comprise rendering the condition metric at the computing system.

3. The computer-readable non-transitory storage medium of claim 2, wherein the rendering comprises providing at least one of a visual representation of the condition metric, an aural representation of the condition metric, or a haptic representation of the condition metric.

4. The computer-readable non-transitory storage medium of claim 2, wherein the rendering comprises rendering the condition metric at a predetermined interior area of the vehicle.

5. The computer-readable non-transitory storage medium of claim 1, wherein accessing the operational information comprises receiving at least a portion of the operational information from one or more sensors of a plurality of sensors, each sensor of the plurality of sensors is configured to detect motion of the vehicle.

6. The computer-readable non-transitory storage medium of claim 1, wherein accessing the behavioral information comprises accessing imaging information indicative of an appearance of the operator of the vehicle.

7. The computer-readable non-transitory storage medium of claim 6, wherein accessing the behavioral information further comprises determining a facial feature of the operator of the vehicle based at least in part on the imaging information, and wherein the determining comprises implementing a facial recognition technique.

8. The computer-readable non-transitory storage medium of claim 6, wherein accessing the behavioral information further comprises accessing audio information indicative of a speech segment uttered by the operator of the vehicle.

9. The computer-readable non-transitory storage medium of claim 8, wherein accessing the behavioral information further comprises determining a verbal feature of the segment speech based at least in part on the audio information, and wherein the verbal feature is representative of the emotional state of the operator.

10. The computer-readable non-transitory storage medium of claim 8, wherein accessing the behavioral information further comprises accessing gesture information indicative of movement of the operator of the vehicle.

11. The computer-readable non-transitory storage medium of claim 1, wherein the operations further comprise supplying, by the computing system, the condition metric to other vehicle, wherein the supplying comprises at least one of transmitting the condition metric wirelessly to the other vehicle or transmitting the condition metric via a link tethered to the other vehicle.

12. The computer-readable non-transitory storage medium of claim 1, wherein the operations further comprise receiving, at the computing system, at least one condition metric from at least one other vehicle, each condition metric of the at least one condition metric is representative of an emotional state of an operator of a respective vehicle of the at least one other vehicle.

13. The computer-readable non-transitory storage medium of claim 12, wherein the operations further comprise rendering the at least one condition metric at the computing system.

14. A computer-readable non-transitory storage medium encoded with computer-accessible instructions that, in response to execution, cause at least one processor to perform operations for vehicular performance management comprising:
   acquiring, at a computing system having at least one processor, a condition metric representative of an emotional state of an operator of a vehicle;
   determining, at the computing system, if the condition metric satisfies a vehicular safety hazard criterion;
   configuring, at the computing system, a vehicle component for a predetermined operation in response to ascertaining that the condition metric satisfies the vehicular safety hazard criterion, wherein the vehicle component includes one or more of a content rendering unit, an in-cabin ambient control unit, or an operation control unit;
   rendering, by the computing system, the condition metric at a predetermined exterior area of the vehicle;
   determining, by the computing system, a travel time for a route between an origin and a destination;

providing a recommendation for the route based at least in part on the behavior of the operator, wherein the route is configured to render within substantially the travel time; and adjusting the condition metric based on the recommendation.

15. The computer-readable non-transitory storage medium of claim 14, wherein the operations further comprise generating information indicative of a route between an origin and a destination, wherein the route is designed to improve the condition metric.

16. A system for vehicular safety, comprising:
at least one memory device having encoded thereon computer-accessible instructions; and
at least one processor functionally coupled to the at least one memory device and configured, by the computer-accessible instructions,
to access operational information indicative of performance of a vehicle;
to access behavioral information indicative of behavior of an operator of the vehicle;
to generate a condition metric representative of an emotional state of the operator based at least in part on at least a portion of the operational information and at least a portion of the behavioral information;
to render the condition metric at a predetermined exterior area of the vehicle;
to determine a travel time for a route between an origin and a destination;
to provide a recommendation for the route based at least in part on the behavior of the operator, wherein the route is configured to render within substantially the travel time; and
to adjust the condition metric based on the recommendation.

17. The system of claim 16, wherein the at least one processor is further configured to render the condition metric at the computing system.

18. The system of claim 17, wherein the at least one processor is further configured to provide at least one of a visual representation of the condition metric, an aural representation of the condition metric, or a haptic representation of the condition metric.

19. The system of claim 18, wherein the at least one processor is further configured to render the condition metric at a predetermined interior area of the vehicle.

20. The system of claim 18, wherein to access the operational information, the at least one processor is further configured to receive at least a portion of the operational information from one or more sensors of a plurality of sensors, each sensor of the plurality of sensors is configured to detect motion of the vehicle.

21. The system of claim 18, wherein to access the behavioral information, the at least one processor is further configured to access imaging information indicative of an appearance of the operator of the vehicle.

22. The system of claim 21, wherein the at least one processor is further configured to determine a facial feature of the operator of the vehicle based at least in part on the imaging information, and wherein the determining comprises implementing a facial recognition technique.

23. The system of claim 21, wherein the at least one processor is further configured to access audio information indicative of a speech segment uttered by the operator of the vehicle.

24. The system of claim 23, wherein the at least one processor is further configured to determine a verbal feature of the segment speech based at least in part on the audio information, and wherein the verbal feature is representative of the emotional state of the operator.

25. The system of claim 23, wherein the at least one processor is further configured to access gesture information indicative of movement of the operator of the vehicle.

26. The system of claim 16, wherein the at least one processor is further configured to supply the condition metric to another vehicle wirelessly or via a link tethered to the another vehicle.

27. The system of claim 16, wherein the at least one processor is further configured to supply the information to infrastructure within an environment of the vehicle.

28. The system of claim 16, wherein the at least one processor is further configured to receive at least one condition metric from at least one other vehicle, each condition metric of the at least one condition metric is representative of an emotional state of an operator of a respective vehicle of the at least one other vehicle.

29. The system of claim 28, wherein the at least one processor is further configured to render the at least one condition metric at the computing system.

* * * * *